(12) United States Patent
Sambandamurthy et al.

(10) Patent No.: US 10,197,645 B2
(45) Date of Patent: Feb. 5, 2019

(54) MULTI-CHANNEL ENDORECTAL COILS AND INTERFACE DEVICES THEREFOR

(71) Applicant: Bayer Medical Care Inc., Indianola, PA (US)

(72) Inventors: Sriram Sambandamurthy, Gibsonia, PA (US); Maged R. Kamel, Allison Park, PA (US); Robert J. McKenney, Indianola, PA (US)

(73) Assignee: Bayer HealthCare LLC, Whippany, NJ (US)

( * ) Notice: Subject to any disclaimer, the term of this patent is extended or adjusted under 35 U.S.C. 154(b) by 769 days.

(21) Appl. No.: 14/874,672

(22) Filed: Oct. 5, 2015

(65) Prior Publication Data

US 2016/0131725 A1     May 12, 2016

Related U.S. Application Data

(62) Division of application No. 13/805,531, filed as application No. PCT/US2011/042354 on Jun. 29, 2011, now Pat. No. 9,817,090.
(Continued)

(51) Int. Cl.
*G01R 33/3415*     (2006.01)
*G01R 33/34*     (2006.01)
(Continued)

(52) U.S. Cl.
CPC .......... *G01R 33/3415* (2013.01); *A61B 5/055* (2013.01); *G01R 33/34084* (2013.01); *G01R 33/365* (2013.01)

(58) Field of Classification Search
CPC .......... G01R 33/3415; G01R 33/34084; G01R 33/365; A61B 5/055
See application file for complete search history.

(56) References Cited

U.S. PATENT DOCUMENTS

| | | | |
|---|---|---|---|
| 4,594,566 A | 6/1986 | Maudsley |
| 4,816,765 A | 3/1989 | Boskamp |

(Continued)

FOREIGN PATENT DOCUMENTS

| | | |
|---|---|---|
| EP | 0385367 A1 | 9/1990 |
| JP | H05115456 A | 5/1993 |

(Continued)

OTHER PUBLICATIONS

Gilderdale, D.J., et al., "Design and use of internal receiver coils for magnetic resonance imaging," The British Journal of Radiology, vol. 72, pp. 1141-1151, The British Institute of Radiology (1999).

(Continued)

*Primary Examiner* — Dixomara Vargas
(74) *Attorney, Agent, or Firm* — James R. Stevenson; Ryan Miller

(57) ABSTRACT

An intracavity probe for use with a magnetic resonance system includes: a pair of coil loops arranged in a phased array configuration; a pair of decoupling circuits; a pair of output cables; and a spacer material positioned adjacent to an anterior surface of the coil loops. Each coil loop has a drive capacitor and a tuning capacitor. Each decoupling circuit is connected across the tuning capacitor of one of the coil loops. Each output cable is connected at a first end thereof across the drive capacitor of one of the coil loops such that each of the drive capacitors is provided with a separate ground. The spacer material assures a predetermined distance between the pair of coil loops and the region of interest, which thereby reduces intensity of the magnetic resonance signals in proximity to the coil loops, maintains SNR at depth within the region of interest and reduces artifacts.

18 Claims, 30 Drawing Sheets

Related U.S. Application Data

(60) Provisional application No. 61/360,646, filed on Jul. 1, 2010.

(51) Int. Cl.
*G01R 33/36* (2006.01)
*A61B 5/055* (2006.01)

(56) References Cited

U.S. PATENT DOCUMENTS

| | | | |
|---|---|---|---|
| 4,887,038 A | 12/1989 | Votruba et al. | |
| 4,918,388 A | 4/1990 | Mehdizadeh et al. | |
| 5,050,607 A | 9/1991 | Bradley et al. | |
| 5,057,778 A | 10/1991 | Rath | |
| 5,307,814 A | 5/1994 | Kressel et al. | |
| 5,348,010 A | 9/1994 | Schnall et al. | |
| 5,355,087 A | 10/1994 | Claiborne et al. | |
| 5,432,449 A | 7/1995 | Ferut et al. | |
| 5,451,232 A | 9/1995 | Rhinehart et al. | |
| 5,476,095 A | 12/1995 | Schnall et al. | |
| 5,585,721 A | 12/1996 | Datsikas | |
| 5,621,323 A | 4/1997 | Larsen | |
| 5,635,928 A | 6/1997 | Takagi et al. | |
| 5,666,055 A | 9/1997 | Jones et al. | |
| 6,249,121 B1 | 6/2001 | Boskamp et al. | |
| 6,294,972 B1 | 9/2001 | Jesmanowicz et al. | |
| 6,297,636 B1 | 10/2001 | Shimo et al. | |
| 6,307,371 B1 | 10/2001 | Zeiger | |
| 6,326,789 B1 | 12/2001 | Yoshida et al. | |
| 6,747,452 B1 | 6/2004 | Jevtic et al. | |
| 6,771,070 B2 | 8/2004 | Lee | |
| 6,798,206 B2 | 9/2004 | Misic | |
| 6,831,460 B2 | 12/2004 | Reisker et al. | |
| 6,914,432 B2 | 7/2005 | Dumoulin et al. | |
| 7,012,430 B2 | 3/2006 | Misic | |
| 7,084,629 B2 | 8/2006 | Monski, Jr. et al. | |
| 7,138,801 B2 | 11/2006 | Yamamoto et al. | |
| 7,141,971 B2 | 11/2006 | Duensing et al. | |
| 7,180,296 B2 | 2/2007 | Gross | |
| 7,233,147 B2 * | 6/2007 | Duensing | G01R 33/34046 324/318 |
| 7,382,132 B1 | 6/2008 | Mathew et al. | |
| 7,446,528 B2 | 11/2008 | Doddrell et al. | |
| 7,692,427 B2 | 4/2010 | Lee et al. | |
| 7,701,209 B1 | 4/2010 | Green | |
| 7,733,088 B2 | 6/2010 | Cho et al. | |
| 7,747,310 B2 | 6/2010 | Misic et al. | |
| 7,885,704 B2 | 2/2011 | Misic | |
| 7,911,209 B2 | 3/2011 | Alradady et al. | |
| 8,193,809 B2 | 6/2012 | Akgun et al. | |
| 8,581,590 B2 | 11/2013 | Misic et al. | |
| 8,749,235 B2 | 6/2014 | Iwama et al. | |
| 8,766,632 B2 | 7/2014 | Biber et al. | |
| 8,866,481 B2 | 10/2014 | Zhu et al. | |
| 8,908,400 B2 | 12/2014 | Lisi et al. | |
| 9,182,463 B2 | 11/2015 | Habara et al. | |
| 9,817,090 B2 * | 11/2017 | Sambandamurthy | G01R 33/34084 |
| 9,817,098 B2 * | 11/2017 | Campagna | G01R 33/36 |
| 2003/0020476 A1 * | 1/2003 | Duensing | G01R 33/34046 324/318 |
| 2003/0023609 A1 | 1/2003 | Della-Libera et al. | |
| 2003/0158475 A1 | 8/2003 | Johnson et al. | |
| 2007/0085634 A1 | 4/2007 | Du et al. | |
| 2009/0076378 A1 | 3/2009 | Misic | |
| 2011/0121833 A1 | 5/2011 | Sambandamurthy et al. | |
| 2014/0167758 A1 * | 6/2014 | Sambandamurthy | G01R 33/34084 324/322 |
| 2015/0091574 A1 * | 4/2015 | Campagna | G01R 33/36 324/318 |

FOREIGN PATENT DOCUMENTS

| | | |
|---|---|---|
| JP | H1066683 A | 3/1998 |
| JP | 2008520286 A | 6/2008 |
| WO | 03098236 A2 | 11/2003 |
| WO | 2006017344 A1 | 2/2006 |
| WO | 2008104895 A1 | 9/2008 |
| WO | 2010021222 A1 | 2/2010 |
| WO | 2010056911 A1 | 5/2010 |

OTHER PUBLICATIONS

Kim, et al_, Prostate MR Imaging at 3T With a Longitudinal Array Endorectal Surface Coil and Phased Array Body Coil Journal of Magnetic Resonance Imaging 27, 2006, 1327-1330.

"Extended European Search Report from EP Application No. 11801358", Jul. 11, 2017.

O.; Kraff et al., "An Eight-Channel Transmit/Receive RF Array for Imaging the Carotid Arteries at 7 Tesla", 2009.

* cited by examiner

LOOP

VERTICAL FIELD

BUTTERFLY COIL

HORIZONTAL FIELD

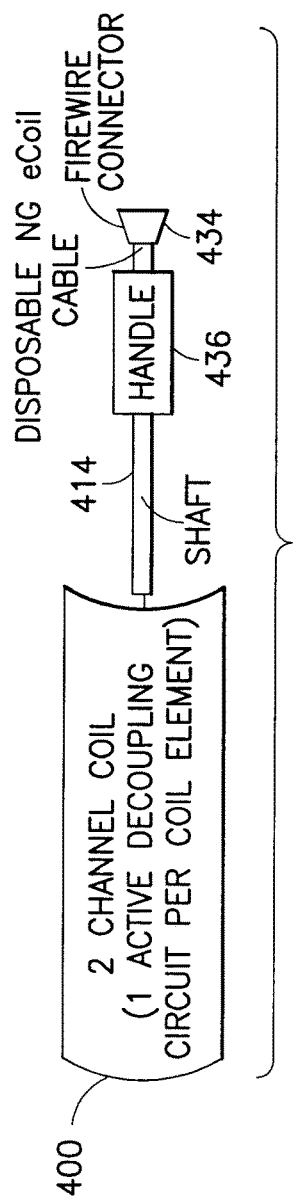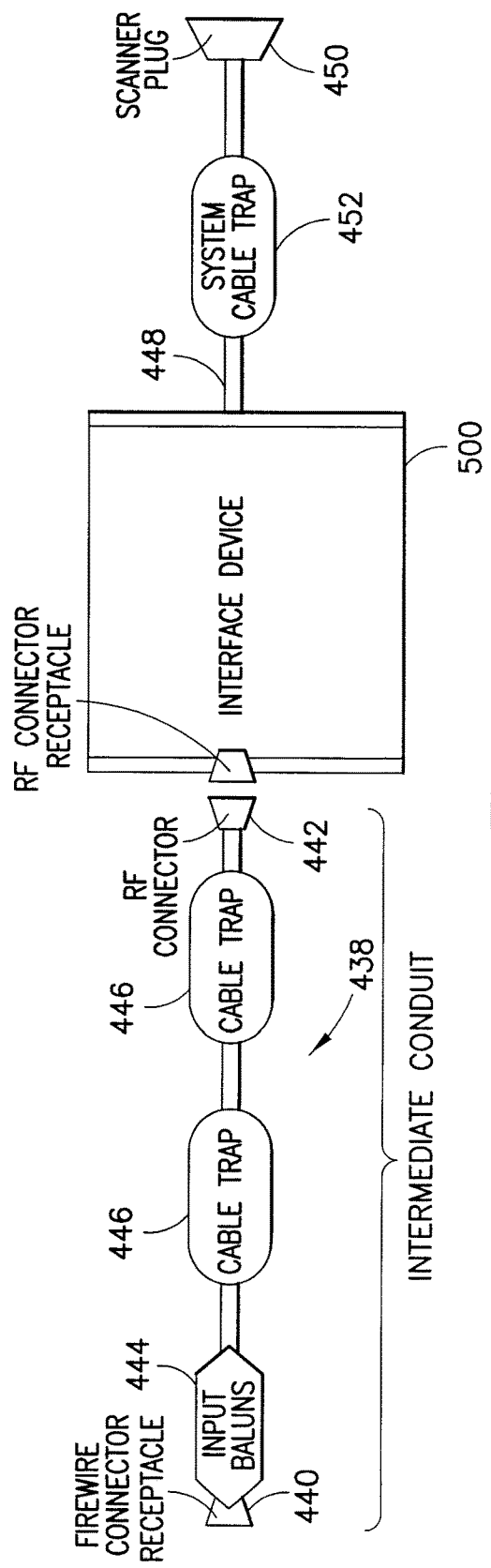
FIG.13A
FIG.13B

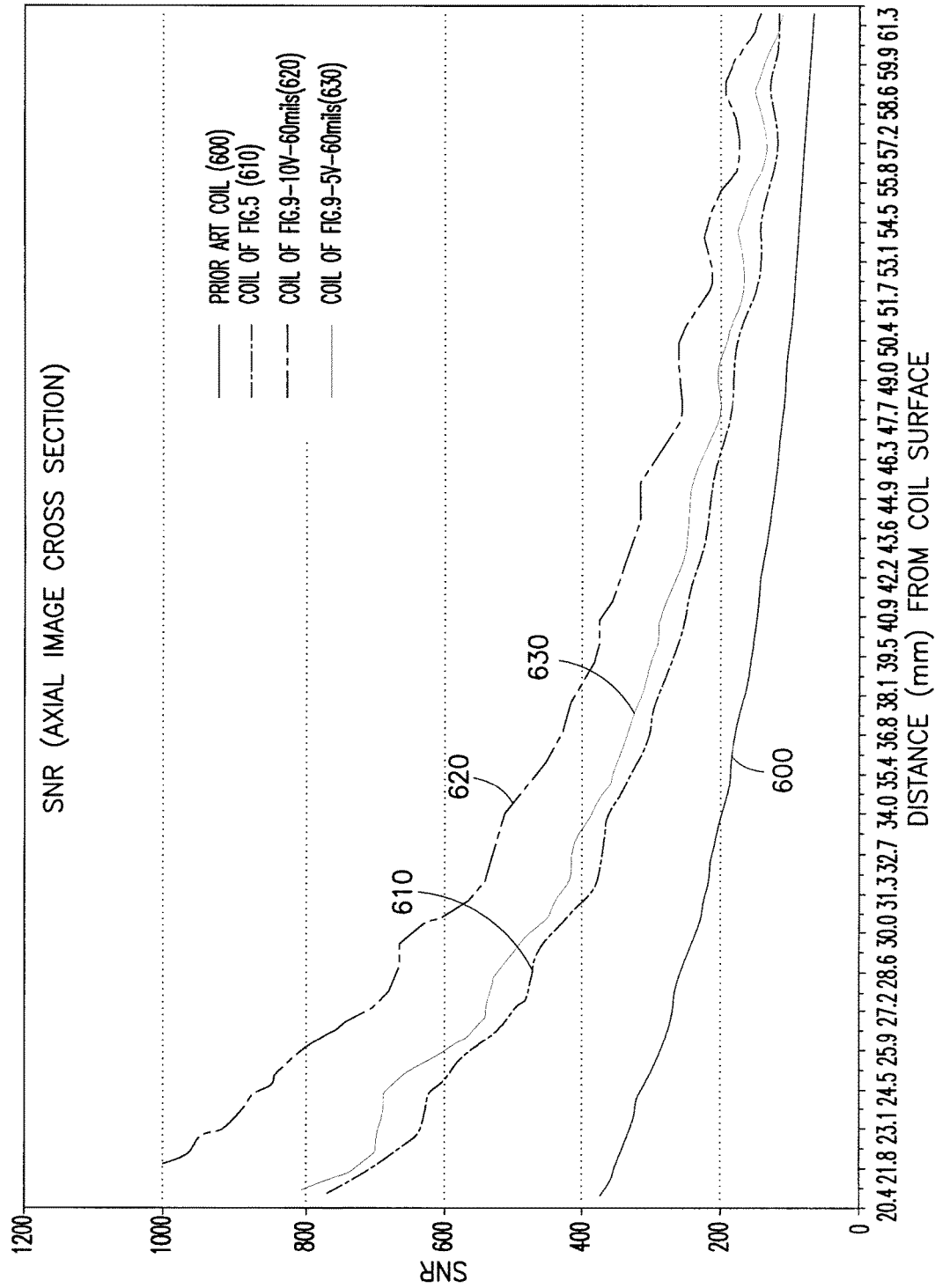

MULTI-CHANNEL ENDORECTAL COILS AND INTERFACE DEVICES THEREFOR

CROSS REFERENCE TO RELATED APPLICATIONS

This application is a Divisional application Ser. No. 13/805,531, filed on Mar. 13, 2013, which is a 371 national phase application of PCT International Application No. PCT/US2011/042354, filed on Jun. 29, 2011, and designating the United States of America, which claims the benefit of U.S. Provisional Application Ser. No. 61/360,646, filed on Jul. 1, 2010, the contents of which are incorporated herein by reference.

BACKGROUND OF THE INVENTION

Field of the Invention

The present invention generally relates to systems and methods of obtaining images and spectra of anatomical structures using magnetic resonance (MR) systems. More particularly, the present invention pertains to multiple embodiments of a multichannel surface coil array and associated interface devices capable of providing images and spectroscopic results from the MR signals obtained from the nuclei excited during MR procedures.

Description of Related Art

The following background information is provided to assist the reader to understand the invention disclosed below and the environment in which it will typically be used. The terms used herein are not intended to be limited to any particular narrow interpretation unless clearly stated otherwise, either expressly or implied, in this document.

Magnetic resonance imaging (MRI) is a noninvasive method of producing high quality images of the interior of the human body. It allows medical personnel to see inside the human body without surgery or the use of ionizing radiation such as X-rays. The images are of such high resolution that cancer and other forms of pathology can often be visually distinguished from healthy tissue. Magnetic resonance techniques and systems have also been developed for performing spectroscopic analyses by which the chemical content of body tissue or other material can be ascertained.

MRI uses a powerful magnet, radio waves, and computer technology to create detailed images of the soft tissues, muscles, nerves, and bones in the body. It does so by taking advantage of a basic property of the hydrogen atom, an atom found in abundance in all cells within living organisms. In the absence of a magnetic field, the nuclei of hydrogen atoms spin like a top, or precess, randomly in every direction. When subject to a strong magnetic field, however, the spin-axes of the hydrogen nuclei align themselves in the direction of the field. This is because the nucleus of the hydrogen atom has what is referred to as a large magnetic moment, a strong inherent tendency to line up with the direction of the field. Collectively, the hydrogen nuclei of the area to be imaged create an average vector of magnetization that points parallel to the magnetic field.

A typical MRI system, or scanner, includes a main magnet, three gradient coils, a radio frequency (RF) antenna (often referred to as the whole body coil), and a computer station from which an operator can control the system. The chief component of the MRI system, however, is the main magnet. It is typically superconducting in nature and cylindrical in shape. Within its bore (an opening into which patients are placed during an MRI procedure), the main magnet generates a strong magnetic field, often referred to as the B0 field, which is both uniform and static (non-varying). This B0 magnetic field is oriented along the longitudinal axis of the bore, referred to as the z direction, which compels the magnetization vectors of the hydrogen nuclei in the body to align themselves parallel to that axis. In this alignment, the nuclei are prepared to receive RF energy of the appropriate frequency from the whole body coil. This frequency is known as the Larmor frequency and is governed by the equation $\omega = \gamma B0$, where $\omega$ is the Larmor frequency (at which the hydrogen atoms precess), $\gamma$ is the gyromagnetic constant, and B0 is the strength of the static magnetic field.

The RF antenna, or whole body coil, is generally used both to transmit pulses of RF energy and to receive the resulting MR signals induced thereby in the hydrogen nuclei. Specifically, during its transmit cycle, the body coil broadcasts RF energy into the cylindrical bore. This RF energy creates a radio frequency magnetic field, also known as the RF B1 field, whose magnetic field lines are directed in a line perpendicular to the magnetization vector of the hydrogen nuclei. The RF pulse causes the spin-axes of the hydrogen nuclei to tilt with respect to the main (B0) magnetic field, thus causing the net magnetization vector to deviate from the z direction by a known angle. The RF pulse, however, will affect only those hydrogen nuclei that are precessing about their axes at the frequency of the RF pulse. In other words, only the nuclei that "resonate" at that frequency will be affected, and such resonance is achieved in conjunction with the operation of the three gradient coils.

The gradient coils are electromagnetic coils. Each gradient coil is used to generate a linearly varying yet static magnetic field along one of the three spatial directions (x, y, z) within the cylindrical bore known as the gradient B1 field. Positioned inside the main magnet, the gradient coils are able to alter the main magnetic field on a very local level when they are turned on and off very rapidly in a specific manner. Thus, in conjunction with the main magnet, the gradient coils can be operated according to various imaging techniques so that the hydrogen nuclei, at any given point or in any given strip, slice, or unit of volume, will be able to achieve resonance when an RF pulse of the appropriate frequency is applied. In response to the RF pulse, the precessing hydrogen atoms in the selected region absorb the RF energy being transmitted from the body coil, thus forcing the magnetization vectors thereof to tilt away from the direction of the main (B0) magnetic field. When the body coil is turned off, the hydrogen nuclei begin to release the RF energy in the form of the MR signal, as explained further below.

One well known technique that can be used to obtain images is referred to as the spin echo imaging technique. Operating according to this technique, the MRI system first activates one gradient coil to set up a magnetic field gradient along the z-axis. This is called the "slice select gradient", and it is set up when the RF pulse is applied and it shuts off when the RF pulse is turned off. It allows resonance to occur only within those hydrogen nuclei located within a slice of the area being imaged. No resonance will occur in any tissue located on either side of the plane of interest. Immediately after the RF pulse ceases, all of the nuclei in the activated slice are "in phase", i.e., their magnetization vectors all point in the same direction. Left to their own devices, the net magnetization vectors of all the hydrogen nuclei in the slice would relax, thus realigning with the z direction. Instead, however, the second gradient coil is briefly activated to create a magnetic field gradient along the y-axis. This is called the "phase encoding gradient". It causes the magnetization vectors of the nuclei within the slice to point, as one moves between the weakest and strongest ends of the gradient, in increasingly different directions. Next, after the RF pulse, slice select gradient, and phase encoding gradient have been turned off, the third gradient coil is briefly activated to create a gradient along the x-axis. This is called the "frequency encoding gradient" or "read out gradient", as it is only applied when the MR signal is ultimately measured. It causes the relaxing magnetization vectors to be differentially re-excited, so that the nuclei near the low end of the gradient begin to precess at a faster rate, and those at the high end pick up even more speed. When these nuclei relax again, the fastest ones (those which were at the high end of the gradient) will emit the highest frequency of radio waves.

Collectively, the gradient coils allow the MR signal to be spatially encoded, so that each portion of the area being imaged is uniquely defined by the frequency and phase of its resonance signal. In particular, as the hydrogen nuclei relax, each becomes a miniature radio transmitter giving out a characteristic pulse that changes over time, depending on the local microenvironment in which it resides. For example, hydrogen nuclei in fats have a different microenvironment than do those in water, and thus transmit different pulses. Due to these differences, in conjunction with the different water-to-fat ratios of dissimilar tissues, different tissues transmit radio signals of different frequencies. During its receive cycle, the body coil detects these miniature radio transmissions, which are often collectively referred to as the MR signal. From the body coil, these unique resonance signals are conveyed to the receivers of the MR system, where they are converted into mathematical data corresponding thereto. The entire procedure must be repeated multiple times to form an image with a good signal-to-noise ratio (SNR). Using multidimensional Fourier transformations, an MR system can convert the mathematical data into a two- or even a three-dimensional image.

When more detailed images of a specific part of the body are needed, a local coil is often used instead of the whole body coil. A local coil can take the form of a volume coil or a surface coil. A volume coil is used to surround or enclose the volume to be imaged (e.g., a head, an arm, a wrist, a leg, or a knee). A surface coil, however, is merely placed upon the surface of a patient so that the underlying region of interest (e.g., the abdominal, thoracic, and/or pelvic regions) can be imaged. In addition, a local coil can be designed to operate either as a receive-only coil or a transmit/receive (T/R) coil. The former is only capable of detecting the MR signals produced by the body in response to an MRI procedure, as noted above. A T/R coil, however, is capable of both receiving the MR signals as well as transmitting the RF pulses that produce the RF B1 magnetic field, which is the prerequisite for inducing resonance in body tissue.

It is well known in the field of MRI to use a single local coil, whether surface or volume, to detect the MR signals. According to the single coil approach, a relatively large local coil is used to cover or enclose the entire region of interest. Early receiving coils were just linear coils, meaning that they could detect only one of the two (i.e., vertical MX' and horizontal MY') quadrature components of the MR signals produced by the region of interest. One example of a linear coil is the single loop coil shown in FIG. 1A. This loop is only capable of detecting magnetic fields (i.e., MR signals) that are oriented perpendicular/vertical to the plane of the loop as shown in FIG. 1B. Another example of a linear coil is the butterfly or saddle coil shown in FIG. 2A. Unlike the single loop, the butterfly coil is only sensitive to magnetic fields that are oriented parallel to the plane of the coil as shown in FIG. 2B. This is because a butterfly coil is constructed by twisting a loop in the middle to form two identical subloops about a midpoint. Because the currents flowing in the subloops are the same but flow in counter-rotating directions, the magnetic flux generated by the current flowing through one subloop of the symmetric structure is equal but opposite to the flux due to the current in the other subloop. Therefore, about the midpoint of the structure, the vertical fields, due to the counter-rotating currents, oppose and thus cancel each other. The horizontal fields generated by those currents, however, combine, yielding a magnetic field that is oriented parallel to the plane of the coil.

Accordingly, receiving coils employing quadrature mode detection, meaning that they could intercept both the vertical and horizontal components, have been developed. Compared to linear receiving coils, quadrature receiving coils enabled MRI systems to provide images for which the SNR was much improved, typically by as much as 41%. Even with the improvement brought with quadrature mode detection, the single coil approach still provided images whose quality invited improvement. The disadvantage inherent to the single coil approach is attributable to just one coil structure being used to acquire the MR signals over the entire region of interest.

Phased array coils were also developed to overcome the shortcomings with the single coil approach. Instead of one large local coil, the phased array approach uses a plurality of smaller local coils, with each such coil covering or enclosing only a portion of the region of interest. In a system having two such coils, for example, each of the coils would cover or enclose approximately half of the region of interest, with the two coils typically being partially overlapped for purposes of magnetic isolation. The two coils would acquire the MR signals from their respective portions simultaneously, and they would not interact adversely due to the overlap. Because each coil covers only half of the region of interest, each such coil is able to receive the MR signals at a higher SNR ratio for that portion of the region of the interest within its coverage area. The smaller local coils of the phased array thus collectively provide the MRI system with the signal data necessary to generate an image of the entire region of interest that is higher in resolution than what can be obtained from a single large local coil.

One example of a phased array coil is the Gore® torso array produced by W.L. Gore and Associates, Inc. The torso array contains four surface coils, two of which are disposed in an anterior paddle, and the other two are disposed in a posterior paddle. The two paddles are designed to be placed against the anterior and posterior surfaces, respectively, of the patient about the abdominal, thoracic, and pelvic regions. The torso array is designed for use with an MR system whose data acquisition system has multiple receivers. The four leads of the torso array, one each from the two anterior surface coils and the two posterior surface coils, can be connected to separate receivers, with each receiver amplifying and digitizing the signal it receives. The MR system then combines the digitized data from the separate receivers to form an image whose overall SNR is better than what could be obtained from a single local coil, or even two larger anterior and posterior local coils, covering the entire region of interest alone.

It is also well known to obtain images of internal bodily structures through the use of intracavity probes. An example of a prior art intracavity probe designed primarily for use with 1.0 T and 1.5 T MR systems can be found in U.S. Pat. Nos. 5,476,095 ('095) and 5,355,087 ('087), both of which are assigned to the assignee of the present invention and incorporated herein by reference. The prior art probe disclosed is designed to be inserted into bodily openings, such as the rectum, vagina, and mouth. These patents also disclose interface devices that are designed to interface the prior art intracavity probe with MR imaging and spectroscopy systems. A method of using the intracavity probe is disclosed in U.S. Pat. No. 5,348,010, which is also assigned to the assignee of the present invention and incorporated herein by reference.

The prior art probe, operated in conjunction with its associated interface unit, allows an MR system to generate images of, and spectroscopic results for, various internal bodily structures, such as the prostate gland, colon, or cervix. Examples of such prior art probes include the BPX-15 prostate/endorectal coil (E-coil), the PCC-15 colorectal coil, and the BCR-15 cervix coil, all of which are part of the eCoil™ line of disposable coils produced by MEDRAD, Inc. of Indianola, Pa. Examples of such interface units include the ATD-II and the ATD-Torso units, also produced by MEDRAD, Inc.

The ATD-II unit is used to interface the prior art probe with one receiver of an MR system to provide images or spectra of the region of interest, namely, the prostate gland, colon, or cervix. The ATD-Torso unit is used to interface not only the prior art probe but also the Gore® torso array with multiple receivers of the MR system. When connected to such a probe and the torso array, the ATD-Torso unit allows the MR system to provide images or spectra not only of the prostate gland, colon, or cervix but also of the surrounding anatomy, i.e., the abdominal, thoracic, and pelvic regions.

U.S. Pat. Nos. 7,747,310 and 7,885,704, both of which are assigned to the assignee of the present invention and incorporated herein by reference, disclose several intracavity probes, and associated interface devices, for use with MR systems designed to operate at higher field strengths than the prior art probes of the '087 and '095 patents. For example, the latter reference teaches a probe having a coil loop that includes two drive capacitors and a tuning capacitor, all of which are in series. Connected across each drive capacitor is an output cable having an electrical length of $S_L+n(\lambda/4)$. When each output cable is connected at its other end to the interface device, the coil loop is thereby interconnected through the interface device to the MR system.

With reference to FIG. 3, quadrature intracavity probes have been developed. For instance, International Patent Application Publication No. WO 2010/056911, which is assigned to the assignee of the present invention and is incorporated herein by reference, discloses a single coil structure that is sensitive to both the vertical and horizontal components of the MR signal by virtue of a simple loop-type coil element and a butterfly-type coil element that share a center conductor. More specifically, the quadrature coil, generally designated 10, includes an outer loop 12, a center conductor 14 bisecting the outer loop 12, and an output line, generally designated 16. The outer loop 12 includes a plurality of capacitors including first and second drive capacitors 18 and 20 and first and second tuning capacitors 22 and 24. Of approximately equal values, the drive capacitors 18, 20 are serially deployed within the outer loop 12 and at their junction node 26 form a virtual ground for electrically balancing and impedance matching the loop. Tuning capacitors 22, 24 are also serially deployed within outer loop 12, with their common node 28 being situated diametrically opposite the junction node 26. Of approximately equal values, the tuning capacitors 22, 24 are selected to resonate the outer loop 12 at the operating frequency of the MR system. In that regard, outer loop 12 is shown in FIG. 3 as having four inductors. The values of those inductors merely represent the inductances inherent in the conductive (e.g., copper) segments of the loop. The output line 16 includes two coaxial cables 30 and 32 with the shield conductor of each connected to the junction node 26 of the coil 10. The center conductor 14 extends between and evenly bisects the junction and common nodes 26 and 28 of outer loop 12, and thus maintains the physical and electrical symmetry of quadrature coil 10. FIG. 3 shows the center conductor 14 as having two inductors and a tuning capacitor 34 symmetrically deployed along its length. Like outer loop 12, the values of those inductors merely represent the inductances inherent in the conductor. The value of the tuning capacitor 34 has been selected so that its reactance at the operating frequency equals the inductive reactance of center conductor 14. This configuration permits the simple loop and butterfly elements of the coil to detect MR signals orthogonal and parallel, respectively, to the plane of the coil.

With reference to FIG. 4 and as disclosed in U.S. Pat. No. 7,885,704, a coil having a phased array configuration for use as in an endorectal probe has been developed. The coil includes four coil loops 40, 41, 42, and 43 deployed in a phased array configuration in which each coil loop 40, 41, 42, and 43 is critically overlapped by its neighbor. Each coil loop 40, 41, 42, and 43 includes a drive capacitor 44, 45, 46, and 47 and a tuning capacitor 48, 49, 50, and 51 arranged diametrically opposite to the drive capacitor 44, 45, 46, and 47. In addition, each coil loop 40, 41, 42, and 43 includes an output line 52, 53, 54, and 55 connected across the respective drive capacitor 44, 45, 46, and 47. Accordingly, a four element, four channel configuration is provided. This arrangement provides a demonstrably higher signal-to-noise ratio (SNR) than the quadrature coil 10 described hereinabove with reference to FIG. 3; however, the coverage is less uniform due to the areas of low signal in the critically-coupled (i.e., overlapped conductor) areas. This non-uniformity is undesirable for use in an endorectal probe due to the higher amounts of non-uniformity proximal to the coil conductors.

Despite their widespread acceptance and good reputation in the marketplace, these prior art intracavity probes and interface devices nevertheless have a few shortcomings. For example, they offer limited coverage, exhibit lower signal-to-noise performance, and generally provide less overall flexibility as compared to the endorectal coil technology discussed hereinafter. It is therefore desirable to provide an endorectal coil array and associated interface device capable of providing greater overall flexibility and higher quality images and spectroscopic results from MR signals obtained from nuclei during MR procedures.

SUMMARY OF THE INVENTION

Therefore, it is an object of the present invention to provide a method and system that overcome some or all of the drawbacks and deficiencies evident in the prior art. More specifically, the endorectal coil array and associated interface devices of the present invention are capable of providing greater overall flexibility and higher quality images and spectroscopic results from MR signals obtained from nuclei during MR procedures.

Accordingly, provided is a coil for use with a magnetic resonance system for obtaining images of a region of interest. The coil includes: (a) a pair of coil loops arranged in a phased array configuration each of which for receiving magnetic resonance signals from the region of interest corresponding thereto; and (b) a spacer material positioned adjacent to an anterior surface of the pair of the coil loops. Each of the coil loops has a drive capacitor and a tuning capacitor with the tuning capacitor having a value selected to resonate the coil loop corresponding thereto at an operating frequency of the magnetic resonance system. The spacer material enables a predetermined distance of between about 0.03 and about 0.06 inches to exist between the pair of coil loops and the region of interest and thereby: (i) reduce intensity of the magnetic resonance signals in proximity of the coil loops; (ii) maintain a signal-to-noise ratio at a depth within the region of interest appropriate to reconstruct the images of the region of interest; and (iii) reduce artifacts in the images inclusive of the Gibbs artifact.

The coil may further include a pair of decoupling circuits each of which connected across the tuning capacitor of one of the coil loops. Each of the decoupling circuits may be an active decoupling circuit, a passive decoupling circuit, or both an active and a passive decoupling circuit. The coil may also further include a pair of output cables each of which connected at a first end thereof across the drive capacitor of one of the coil loops such that each of the drive capacitors is provided with a separate ground. An intermediate conduit may be provided that includes: (a) an input connector; (b) an output connector; (c) pair of internal cables for connecting at one end thereof, respectively, to the output cables of the intracavity probe via the input connector and approximate another end thereof to an interface device for the intracavity probe via the output connector; (d) a pair of baluns each of which interconnected between an end of one of the internal cables and at least one of the input connector and the output connector; and (e) at least one cable trap connected thereabout.

The phased array configuration may require the pair of coil loops to be critically overlapped, to share a common conductor, or to be arranged in a hybrid overlap configuration wherein at least a portion of each of the coil loops is overlapped and the coil loops share a common conductor.

A passive decoupling circuit may be provided at a second end of each of the output cables. Each of the passive decoupling circuits may include series connected back-to-back diodes and a reactance component. The reactance component may be at least one of an inductor and a capacitor.

The coil may be provided as part of an intracavity probe or may be a surface coil. The surface coil may be a head coil, a torso coil, a neck coil, a limb coil, or any combination thereof.

Also provided is an intracavity probe for use with a magnetic resonance system for obtaining images of a region of interest within a cavity of a patient. The intracavity probe includes: (a) a pair of coil loops arranged in a phased array configuration each of which receive magnetic resonance signals from the region of interest corresponding thereto; (b) a pair of decoupling circuits each of which connected across the tuning capacitor of one of the coil loops; (c) a pair of output cables each of which connected at a first end thereof across the drive capacitor of one of the coil loops such that each of the drive capacitors is provided with a separate ground; and (d) a spacer material positioned adjacent to an anterior surface of the pair of the coil loops. Each of the coil loops includes a drive capacitor and a tuning capacitor with the tuning capacitor having a value selected to resonate the coil loop corresponding thereto at an operating frequency of the magnetic resonance system. The spacer material enables a predetermined distance of between about 0.03 and about 0.06 inches to exist between the pair of coil loops and the region of interest and thereby: (i) reduce intensity of the magnetic resonance signals in proximity of the coil loops; (ii) maintain a signal-to-noise ratio at a depth within the region of interest appropriate to reconstruct the images of the region of interest; and (iii) reduce artifacts in the images or spectra inclusive of the Gibbs artifact when the intracavity probe is inserted into the cavity of the patient during acquisition of the images.

Each of the decoupling circuits may be an active decoupling circuit, a passive decoupling circuit, or both an active and a passive decoupling circuit. An intermediate conduit may be provided that includes: (a) an input connector; (b) an output connector; (c) a pair of internal cables for connecting at one end thereof, respectively, to the output cables of the intracavity probe via the input connector and approximate another end thereof to an interface device for the intracavity probe via the output connector; (d) a pair of baluns each of which are interconnected between an end of one of the internal cables and at least one of the input connector and the output connector; and (e) at least one cable trap connected thereabout.

The phased array configuration may require the pair of coil loops to be critically overlapped, to share a common conductor, or to be arranged in a hybrid overlap configuration wherein at least a portion of each of the coil loops is overlapped and the coil loops share a common conductor.

A passive decoupling circuit may be provided at a second end of each of the output cables. Each of the passive decoupling circuits may include series connected back-to-back diodes and a reactance component. The reactance component may be at least one of an inductor and a capacitor.

In addition, provided is an interface device for interfacing a coil comprising a pair of coil loops arranged in a phased array configuration each of which receive magnetic resonance signals from a region of interest corresponding thereto with a magnetic resonance system. The interface device includes: (a) a first preamplifier for receiving a signal from a first coil loop of the pair of coil loops to produce a first amplified signal; (b) a second preamplifier for receiving a signal from a second coil loop of the pair of coil loops to produce a second amplified signal; (c) a first splitter operatively connected to the first preamplifier for dividing the first amplified signal into a right loop signal that is provided to a first channel output and a first composite signal; (d) a second splitter operatively connected to the second preamplifier for dividing the first amplified signal into a left loop signal that is provided to a second channel output and a second composite signal; (e) a third splitter operatively connected to the first splitter for dividing the first composite signal; (f) a fourth splitter operatively connected to the second splitter for dividing the second composite signal; (g) a zero degree combiner operatively connected to the third splitter and the fourth splitter for combining signals received therefrom to produce a saddle or butterfly signal that is provided to a third channel output; and (h) a 180 degree combiner operatively connected to the third splitter and the fourth splitter for combining signals received therefrom to produce a whole loop signal that is provided to a fourth channel output. The interface device is configured to selectively recognize each of the first, second, third, and fourth channel outputs, thereby allowing the magnetic resonance system coupled to the interface device to produce images in a plurality of different modes.

The first preamplifier and the second preamplifier may be provided with a predetermined reduced supply voltage as compared to a rated supply voltage of the first preamplifier and the second preamplifier. At least one attenuator may provide an attenuation nominally in the range of 3 dB to 6 dB. The at least one attenuator may be positioned at at least one of (a) between the first preamplifier and the first splitter; (b) between the second preamplifier and the second splitter; (c) after the first splitter; and (d) after the second splitter. The plurality of modes include, but are not limited to, Left Loop, Right Loop, Whole Loop, Whole Saddle, Right Loop and Left Loop (LL), Whole Loop and Whole Saddle, and Right Loop, Left Loop, Whole Loop, Whole Saddle (LLLS).

Also provided is a system for obtaining images of a region of interest. The system includes: (a) an intracavity probe; and (b) an interface device for interfacing the intracavity probe with a magnetic resonance system. The intracavity probe includes: (i) a pair of coil loops arranged in a phased array configuration each of which receive magnetic resonance signals from the region of interest corresponding thereto; (ii) a pair of output cables each of which connected at a first end thereof across the drive capacitor of one of the coil loops such that each of the drive capacitors is provided with a separate ground; and (iii) a spacer material positioned adjacent to an anterior surface of the pair of the coil loops. Each of the coil loops has a drive capacitor and a tuning capacitor with the tuning capacitor having a value selected to resonate the coil loop corresponding thereto at an operating frequency of the magnetic resonance system. The spacer material enables a predetermined distance of between about 0.03 and about 0.06 inches to exist between the pair of coil loops and the region of interest and thereby reduce intensity of the magnetic resonance signals in proximity of the coil loops, maintain a signal-to-noise ratio at a depth within the region of interest appropriate to reconstruct the images of the region of interest, and reduce artifacts in the images or spectra inclusive of the Gibbs artifact when the intracavity probe is inserted into the cavity of the patient during acquisition of the images. The interface device includes: (i) a first preamplifier for receiving a signal from a first coil loop of the pair of coil loops to produce a first amplified signal; (ii) a second preamplifier for receiving a signal from a second coil loop of the pair of coil loops to produce a second amplified signal; (iii) a first splitter operatively connected to the first preamplifier for dividing the first amplified signal into a right loop signal and a first composite signal; (iv) a second splitter operatively connected to the second preamplifier for dividing the first amplified signal into a left loop signal and a second composite signal; (v) a third splitter operatively connected to the first splitter for dividing the first composite signal; (vi) a fourth splitter operatively connected to the second splitter for dividing the second composite signal; (vii) a zero degree combiner operatively connected to the third splitter and the fourth splitter for combining signals received therefrom to produce a saddle signal; and (viii) a 180 degree combiner operatively connected to the third splitter and the fourth splitter for combining signals received therefrom to produce a whole loop signal.

The first preamplifier and the second preamplifier are provided with a predetermined reduced supply voltage as compared to a rated supply voltage of the first preamplifier and the second preamplifier. The interface device may further include at least one attenuator providing an attenuation nominally in the range of 3 dB to 6 dB. The at least one attenuator may be positioned at at least one of: (a) between the first preamplifier and the first splitter; (b) between the second preamplifier and the second splitter; (c) after the first splitter; and (d) after the second splitter.

The coil may further include a pair of decoupling circuits each of which connected across the tuning capacitor of one of the coil loops. Each of the decoupling circuits may be an active decoupling circuit, a passive decoupling circuit, or both an active and a passive decoupling circuit. An intermediate conduit may be provided that includes: (a) an input connector; (b) an output connector; (c) a pair of internal cables for connecting at one end thereof, respectively, to the output cables of the intracavity probe via the input connector and approximate another end thereof to an interface device for the intracavity probe via the output connector; (d) a pair of baluns each of which interconnected between an end of one of the internal cables and at least one of the input connector and the output connector; and (e) at least one cable trap connected thereabout.

The phased array configuration may require the pair of coil loops to be critically overlapped, to share a common conductor, or to be arranged in a hybrid overlap configuration wherein at least a portion of each of the coil loops is overlapped and the coil loops share a common conductor. A passive decoupling circuit may be provided at a second end of each of the output cables. Each of the passive decoupling circuits may include series connected back-to-back diodes and a reactance component. The reactance component may be at least one of an inductor and a capacitor.

In addition, provided is a coil for use with a magnetic resonance system for obtaining images of a region of interest. The coil includes: (a) a plurality of coil loops arranged in a phased array configuration each of which receive magnetic resonance signals from the region of interest corresponding thereto; (b) a plurality of output cables each of which connected at a first end thereof across the drive capacitor of one of the coil loops; and (c) at least one passive decoupling circuit provided at a second end of each of the output cables. Each of the coil loops has a drive capacitor and a tuning capacitor with the tuning capacitor having a value selected to resonate the coil loop corresponding thereto at an operating frequency of the magnetic resonance system.

A spacer material may be positioned adjacent to an anterior surface of the pair of the coil loops. The spacer material enables a predetermined distance of between about 0.03 and about 0.06 inches to exist between the pair of coil loops and the region of interest and thereby reduce intensity of the magnetic resonance signals in proximity of the coil loops, maintain a signal-to-noise ratio at a depth within the region of interest appropriate to reconstruct the images of the region of interest, and reduce artifacts in the images or spectra inclusive of the Gibbs artifact.

Each of the passive decoupling circuits may include series connected back-to-back diodes and a reactance component. The reactance component may be at least one of an inductor and a capacitor.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

BRIEF DESCRIPTION OF THE DRAWINGS

FIGS. 13A and 13B are block diagrams illustrating the coil of FIG. 12 connected to an interface device in accordance with the present invention;

FIG. 23 is a graph comparing the signal-to-noise ratios (SNR) of the various coil configurations.

DETAILED DESCRIPTION OF THE PREFERRED EMBODIMENTS

Figure 1A:
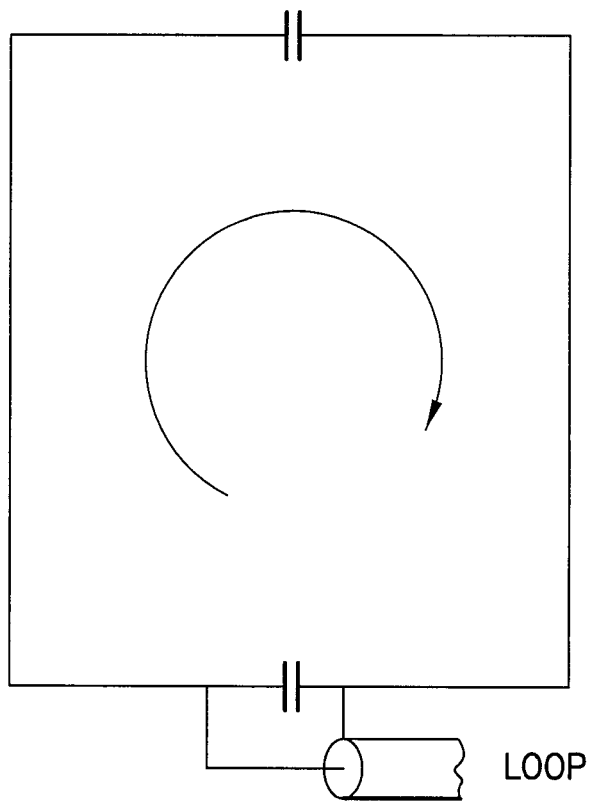
FIG. 1A is a schematic diagram of a conventional single loop coil and FIG. 1B is a representation of the vertically oriented magnetic fields it is capable of sensing.
Figure 1B:
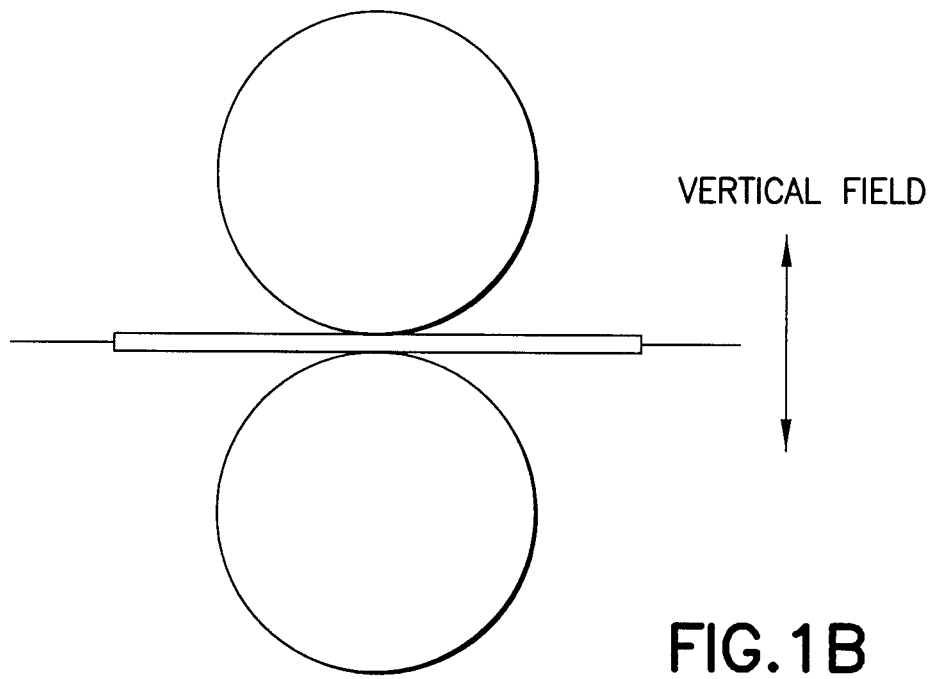

For purposes of the description hereinafter, the terms "upper", "up", "lower", "down", "right", "left", "vertical", "orthogonal", "horizontal", "top", "bottom", "lateral", "longitudinal", and derivatives thereof shall relate to the invention as it is oriented in the drawing figures and/or from the perspective of a patient during a procedure. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

In all of its embodiments and related aspects, the present invention disclosed below is ideally used with magnetic resonance (MR) systems designed to operate at 1.0, 1.5, or 3.0 Tesla or any field strength in between, though it is also applicable to those operable at lower or higher field strengths. The technology is also applicable to scanner configurations with horizontal or vertical bore magnets or other orientations and in closed or open bore scanners.

Figure 5:
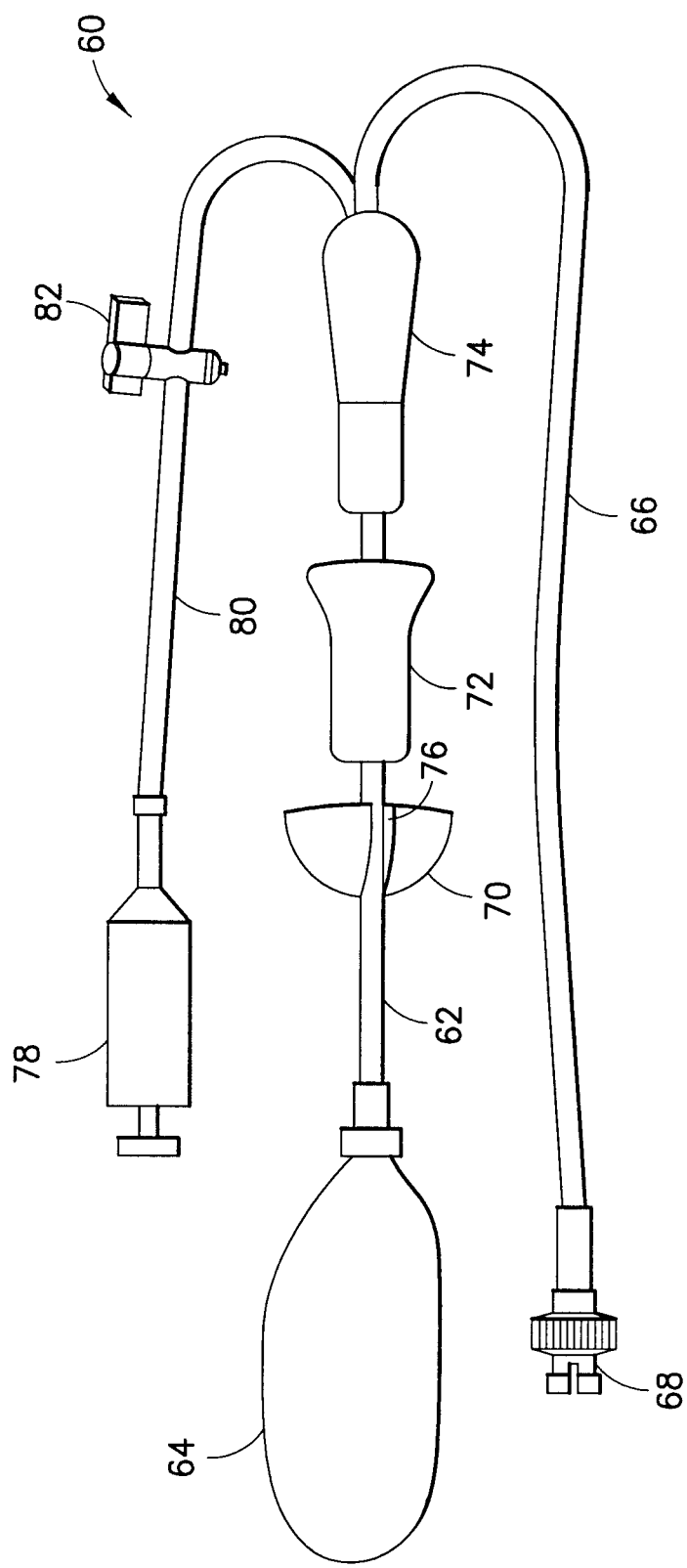
FIG. 5 is a perspective view of an intracavity probe in accordance with the present invention.

The coils discussed hereinafter may be incorporated into an intracavity probe, such as the endorectal probe 60 illustrated in FIG. 5. The intracavity probe 60 includes a flexible shaft 62 and a balloon structure 64. The coils discussed hereinafter in greater detail are attached to an anterior surface of the balloon structure 64. The balloon structure 64 is configured to position the coil in operative proximity to a rectal prostatic bulge of a patient when the balloon structure 64 is inflated, which optimizes the coupling between coil and the target anatomy. The balloon structure 64 is preferably made of a medical-grade latex or other appropriate elastomeric material. Such material should, of course, be non-paramagnetic and exhibit low dielectric losses. The flexible shaft 62 defines two lumens (not shown) therein. Within its cylindrical wall near its distal end, the shaft 62 also defines a hole (not shown) in communication with one of the lumens. This lumen and hole together serve as a passageway for the fluid (e.g., gas or liquid) pumped into and expelled out of balloon structure 64 when inflated and deflated, respectively. Further away from its distal end, the shaft 62 defines another hole in its cylindrical wall. The other lumen and this hole act as the conduit through which the output cables are routed from the coil. The output cables may be housed in a single sheath 66 having a plug 68 at a proximal end thereof to connect the intracavity probe 60 with an appropriate interface device as discussed in greater detail hereinafter.

The intracavity probe 60 further includes an anti-migration disc 70 and a handle 74. Fixed to the proximal end of shaft 62, the handle 74 enables the probe 60 to be easily manipulated at its distal end and, inclusive of balloon structure 64 secured thereon, is inserted into the rectum and appropriately aligned within the cavity as described below. The anti-migration disc 70, composed of a semi-rigid plastic or other suitable polymer, is desirably semi-spherical in shape. As shown in FIG. 5, the disc 70 defines a slot 76. This slot 76 allows the disc 70 to be snapped onto the shaft 62. When affixed to the shaft 62 adjacent the anal sphincter after the probe 60 has been inserted into the rectum, the anti-migration disc 70 prevents the probe 60 from migrating superiorly due to the normal peristaltic activity of the colon.

The intracavity probe 60 also includes a means for controlling inflation of balloon structure 64. The inflation control means desirably takes the form of a syringe 78, a tube 80, and a stop cock 82. The tube 80 connects the syringe 78 to the lumen for fluid of the shaft 62 at the proximal end of the shaft 62. The stop cock 82 is connected in series with the tube 80 and serves to control whether air is pumped to or released from the balloon structure 64.

In operation, the distal end of the intracavity probe 60 is inserted into the cavity via the rectum while the balloon structure 64 is in the uninflated state. With the distal end inserted, the probe 60 is positioned both rotationally and longitudinally within the cavity adjacent the region of interest. Once the intracavity probe 60 is correctly positioned, the anti-migration disc 70 can then be snapped onto the shaft 62 adjacent the sphincter to assure that the intracavity probe 60 stays in position during the MR scanning procedure.

Before inflating the balloon structure 64, the stop cock 82 must be switched to the open state. By utilizing the syringe 78, the balloon structure 64 will inflate via tube 80, stop cock 82, and the lumen for fluid in the shaft 62. As the balloon structure 64 inflates, an outer surface thereof is forced to abut against a wall of the cavity opposite the region of interest, thereby positioning the coil approximate the prostate gland for optimal reception of the MR signals therefrom during the MR scanning procedure. The stop cock 82 can then be switched to the closed position. The intracavity probe 60 can then be connected to the appropriate interface device via the plug 68 of the sheath 66.

When the scanning procedure is completed, the clinician need only switch the stop cock 82 to the open position to deflate the balloon structure 64. Whether or not the anti-migration disc 70 is removed from shaft 62, the distal end can then be removed from the rectum merely by gently pulling on the handle 74 of the intracavity probe 60.

Although the invention is described hereinabove and hereinafter in a specific implementation, i.e., as an endorectal coil array, which is capable of being incorporated within a suitable housing to form an intracavity probe insertable into the rectum to obtain images and/or spectra of the male prostate gland, it should be understood that the invention is equally capable of being adapted to obtain images of and/or spectra from other regions of interest, such as those accessible through the mouth, the vagina, or other orifices penetrable by an intracavity probe. It should also be apparent that the principles presented herein may also be applied to a wide variety of surface coil arrays, such as those intended for imaging of the head, neck, torso, limbs, and other structures of the body.

In general, the endorectal coils disclosed herein include a two element layout that has been configured to receive radio frequency (RF) currents from the whole geometry and, using appropriate splitters and combiners in an interface device discussed hereinafter, turned into a four channel output device.

Figure 6:
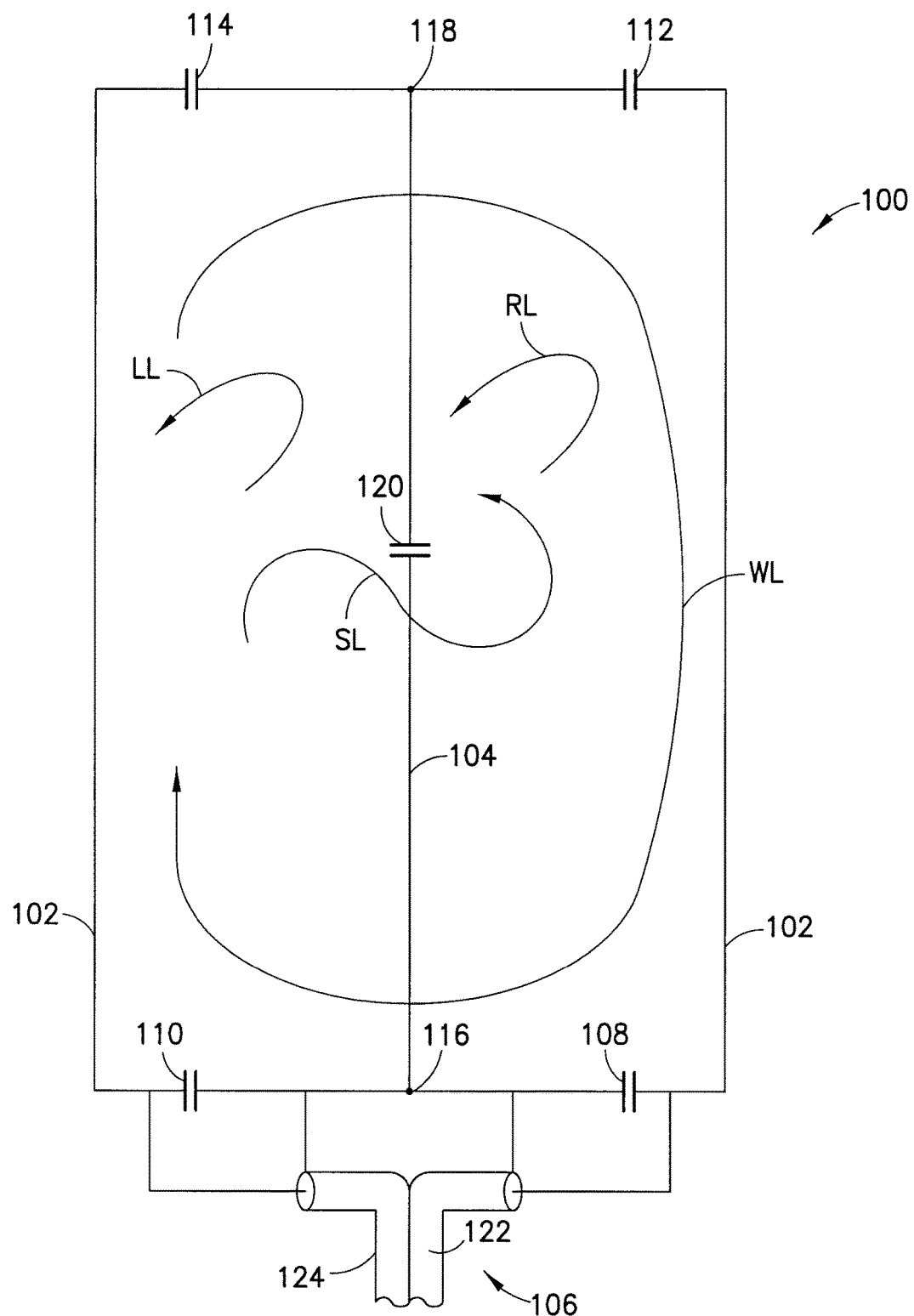
FIG. 6 is a schematic diagram of a coil in accordance with a first embodiment of the present invention.

With reference to FIG. 6, various aspects of a first embodiment of the endorectal coil array are illustrated. More specifically, FIG. 6 illustrates a schematic diagram of a prototype of the first embodiment of the endorectal coil array built for operation with 1.5 T MRI scanners.

The endorectal coil, generally designated 100, includes an outer loop 102, a center conductor 104 bisecting outer loop 102, and an output line, generally designated 106. The outer loop 102 includes a plurality of capacitors including first and second drive capacitors 108 and 110 and first and second tuning capacitors 112 and 114. Of approximately equal values, the drive capacitors 108 and 110 are serially deployed within the outer loop 102 and at their junction node 116 form a virtual ground for electrically balancing and impedance matching the loop. Tuning capacitors 112 and 114 are also serially deployed within outer loop 102, with their common node 118 being situated diametrically opposite the junction node 116. Of approximately equal values, the tuning capacitors 112 and 114 are selected to resonate the outer loop 102 at the operating frequency of the MR system.

In this manner, the outer loop 102 of FIG. 6 has been tuned to detect MR signals emanating from the patient at the operating frequency of a 1.5 T MR system. The shape of outer loop 102 dictates that the loop is capable of detecting only those MR signals whose field lines are oriented vertical to the plane of the loop. The aforementioned tuning scheme, however, also imposes a 180 degree phase shift upon the resulting voltage signals output by outer loop 102 representative of the vertically oriented MR signals it detects. Specifically, relative to the virtual ground at junction node 116, the phase of the voltage signals detectable across the first drive capacitor 108, i.e., at a first port, is 180 degrees from the phase of the voltage signals detectable across the second drive capacitor 110, i.e., at a second port.

The center conductor 104 extends between and evenly bisects the junction and common nodes 116 and 118 of outer loop 102, and thus maintains the physical and electrical symmetry of the coil 100. FIG. 6 shows the center conductor 104 as having a tuning capacitor 120 deployed along its length. The value of the tuning capacitor 120 has been selected so that its reactance at the operating frequency equals the inductive reactance of center conductor 104. This permits two modes of operation to occur simultaneously. First, the equal inductive and capacitive reactances enable center conductor 104 to act as an open circuit relative to outer loop 102. In such an instance, a first channel output representative of the whole loop (shown by arrow WL) is provided.

Beyond acting as an open circuit for outer loop 102 to enable detection of the vertical components of the MR signal, the center conductor 104 also operates with outer loop 102 to emulate a butterfly-type or saddle-type coil for detecting MR signals oriented parallel to the plane of the coil 100. The tuning scheme of the present invention creates not only a simple loop current path for outer loop 102 but also an alternative current path (involving counter-rotating currents) for the outer loop 102 and the center conductor 104 combined. Specifically, during the receive cycle and starting near junction node 116, the current induced by the horizontally-oriented MR signals flows across the second drive capacitor 110 up to the far end of outer loop 102 and into and down to center conductor 104. It then crosses the midpoint of the butterfly or saddle structure and flows across the first drive capacitor 108 up to the far end of outer loop 102 and into and down to center conductor 104 to start the cycle anew as long as the coil 100 is in position to detect MR signals during the receive cycle of operation. In such an instance, a second channel output representative of the saddle/butterfly mode (shown by arrow SL) is provided.

The output line 106 for the coil 100 can be implemented using various mechanisms such as coaxial cable, stripline, microstrip, or other transmission line technologies. FIG. 6 shows two coaxial cables 122 and 124 with the shield conductor of each connected to the junction node 116 of the coil. The center conductor of cable 122 connects to the other side of the first drive capacitor 108, while the center conductor of cable 124 connects to the other side of the second drive capacitor 110. The output line 106 should have an electrical length of $S_L+n(\lambda/4)$ for the reasons disclosed in U.S. Patent Application Publication No. 2009/0076378. $\lambda$ is the wavelength of the operating frequency of the MR system and n is an odd integer whose value will typically be (and is hereinafter treated as being) equal to 1 as the coil 100 will in practice always be reasonably close to the interface device to which it will connect. $S_L$ represents an additional length whose inductive reactance is of the same magnitude as the reactance of each of the first and second drive capacitors 108, 110 across which the terminals of output line 106 connect. With a standard plug accommodating the conductors of both cables, for instance, the center and shield conductors of each cable 122 and 124 connect to a suitable socket or other type connector for the interface device.

In addition, based on an RF splitter configuration of the interface device discussed hereinafter, two channels may also be provided to obtain a left loop signal (shown as arrow LL in FIG. 6) and a right loop signal (shown as arrow RL in FIG. 6) with the center conductor 104 serving as a common conductor for both the loops.

During trial tests of the coil 100, it was determined that the signal-to-noise ratio (SNR), while superior to current endorectal coils, was not as high as desired. In addition, the images obtained using this coil 100 produced unsatisfactory ghosting artifacts as will be discussed in greater detail hereinafter.

Figure 7:
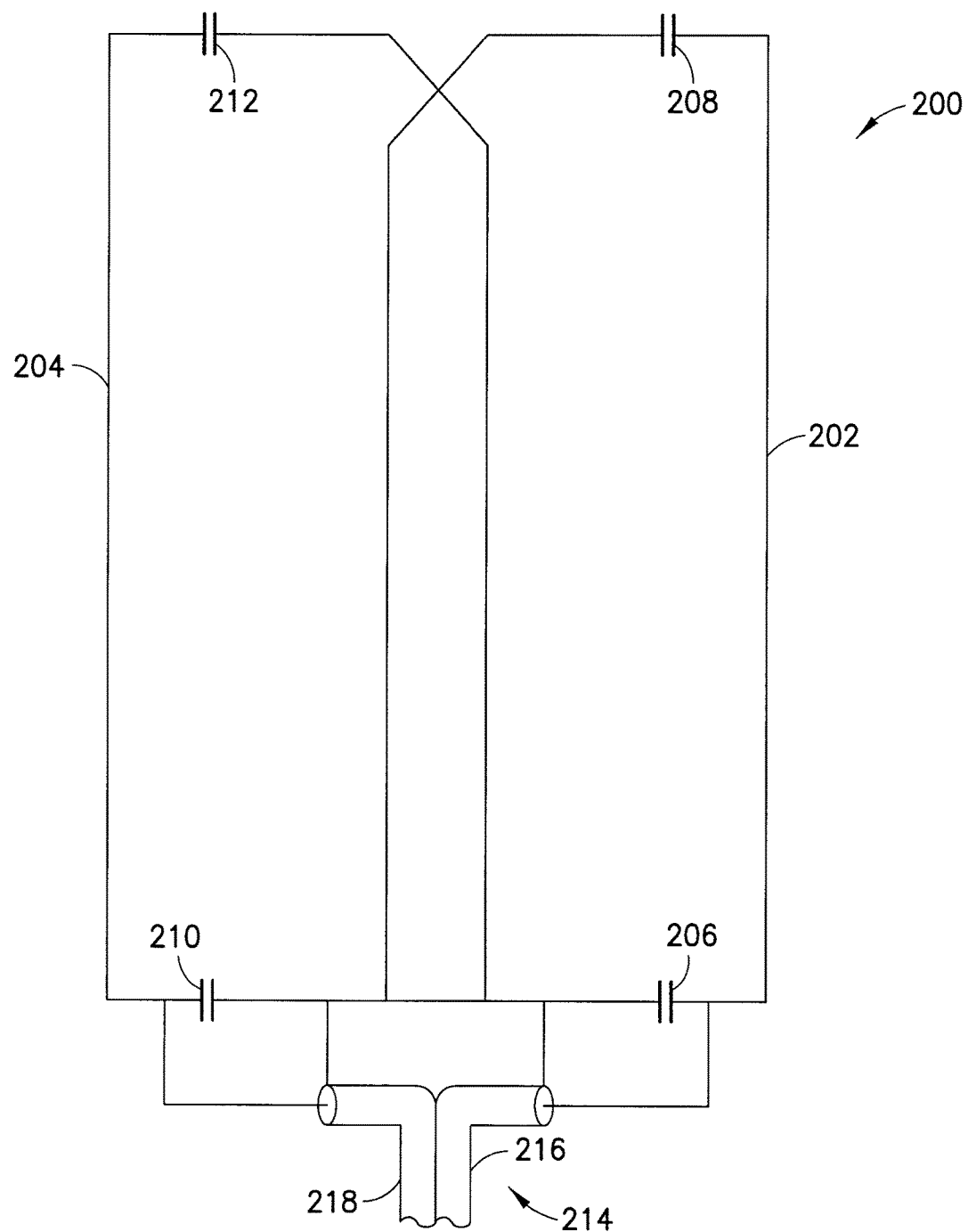
FIG. 7 is a schematic diagram of a coil in accordance with a second embodiment of the present invention.

Accordingly, a second embodiment of the coil was developed in an attempt to obtain a higher SNR. With reference to FIG. 7, this coil, generally designated 200, includes a first coil loop 202 and a second coil loop 204. The pair of coil loops 202 and 204 is arranged in a phased array configuration each of which receive MR signals from the region of interest corresponding thereto. The first coil loop 202 includes a drive capacitor 206 and a tuning capacitor 208. The tuning capacitor 208 has a value selected to resonate the first coil loop 202 at the operating frequency of the MR system. The second coil loop 204 includes a drive capacitor 210 and a tuning capacitor 212. The tuning capacitor 212 has a value selected to resonate the second coil loop 204 at the operating frequency of the MR system.

The coil 200 also includes an output line 214 that includes two coaxial cables 216 and 218. The first coaxial cable 216 is connected at a first end thereof across the first drive capacitor 206 and the second coaxial cable 218 is connected at a first end thereof across the second drive capacitor 210, such that each of the drive capacitors 206 and 210 share a common ground. This configuration can be referred to as a hybrid overlap configuration. A standard plug accommodates the conductors of both cables at a second end thereof, for instance, the center and shield conductors of each cable 216 and 218, such that the output line 214 can be connected to a suitable socket or other type of connector for the interface device. The output line 214 should also have an electrical length of $S_L+n(\lambda/4)$ for the reasons discussed hereinabove.

Accordingly, the second embodiment of coil 200 also includes two elements (i.e., first coil loop 202 and second coil loop 204) and is configured to provide a four channel output. More specifically, coil 200 is configured to provide a first channel output representative of the whole loop, and a second channel output representative of the saddle/butterfly mode. In addition, based on an RF splitter configuration of the interface device discussed hereinafter, a third channel output may be provided to obtain a left loop signal, and a fourth channel output may be provided to obtain a right loop signal.

However, during trial tests of the coil 200, while the SNR of this coil configuration was improved as compared to the first embodiment of coil 100, the images obtained using this coil 200 continued to produce unsatisfactory ghosting artifacts.

An unwanted byproduct of the endorectal coils illustrated in FIGS. 6 and 7 in typical use is excessive signal intensity near the coil conductor, due to the close proximity of the coil conductor to the tissues of the rectal wall. This signal intensity far exceeds typical signal levels in the analog signal path, and can lead to undesirable effects, including the Gibbs artifact, which can manifest itself as "ghosting" of the image, even if the subject is motionless. This artifact differs between scanner manufacturers, due to varying degrees of post-processing employed, and tends to be more apparent on older scanners and signal processing systems. Other effects include signal saturation, where the contrast near the coil conductor is minimal, and thus no clinically useful image detail is available.

Figure 8:
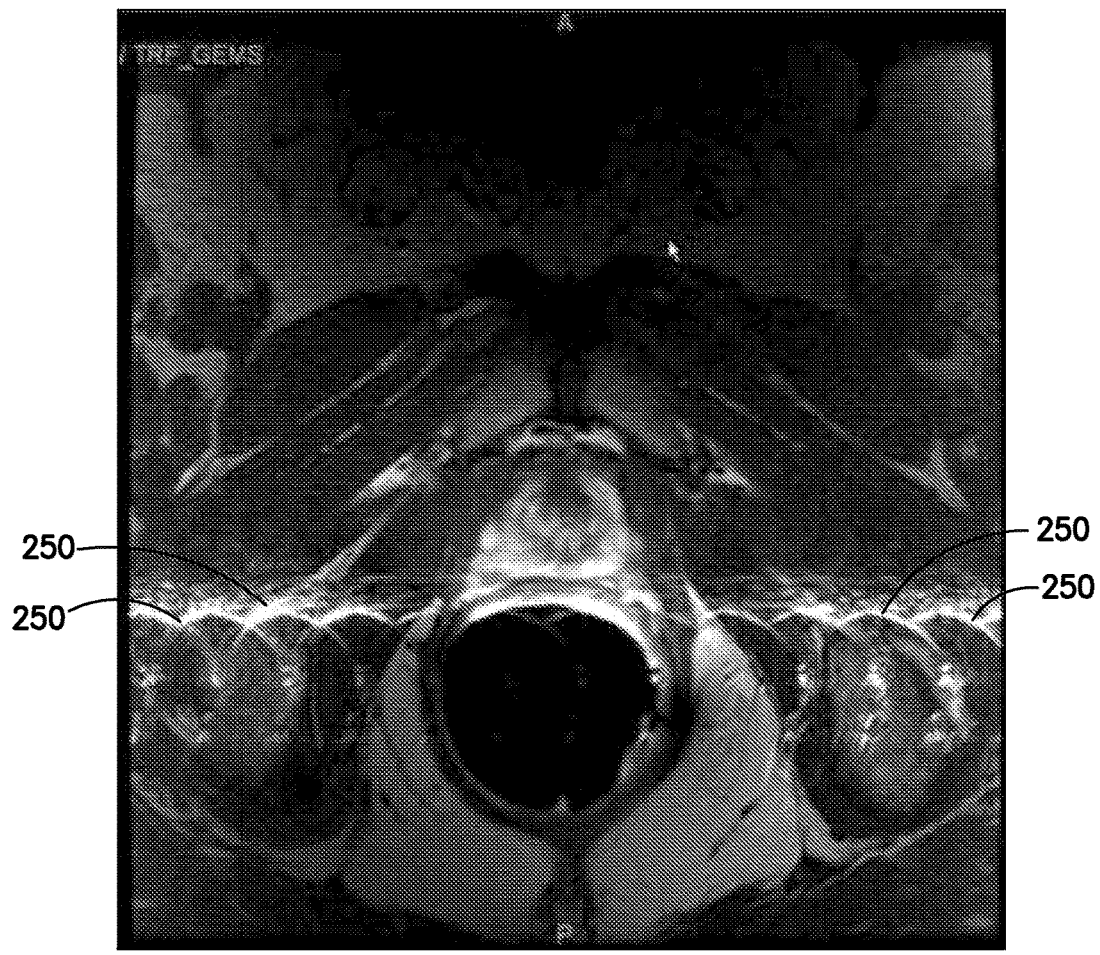
FIG. 8 is an exemplary image produced by an MR system using the coil of FIG. 6 illustrating the ghosting artifacts produced in the image.

With reference to FIG. 8, an exemplary image produced by an MR system using the coil of FIG. 6 or FIG. 7 illustrating the ghosting artifacts produced in the image is provided. These ghosting artifacts 250 appear as small, light rings emanating from the position where the coil is provided. Ghosting artifacts are also referred to as "motion artifacts" in literature. However, these artifacts are produced in images provided using the coils of FIGS. 6 and 7 even in the absence of motion. These artifacts can be classified as "Gibbs artifacts" or edge/transition/ringing artifacts since they are observed due to the Gibbs phenomenon when there is a sudden or abrupt shift/jump in a signal level at the input stage of the image processing.

The Gibbs phenomenon, named after the American physicist J. Willard Gibbs, is the peculiar manner in which the Fourier series of a piecewise continuously differentiable periodic function behaves at a jump discontinuity. The Gibbs phenomenon can be seen as the result of convolving a Heaviside step function (if periodicity is not required) or a square wave (if periodic) with a sinc function. The oscillations in the sinc function cause the ripples in the output.

In MR imaging, the Gibbs phenomenon causes artifacts in the presence of adjacent regions of markedly differing signal intensity. Gibbs artifacts are bright or dark lines that are seen parallel and adjacent to borders of abrupt intensity change (see element 250 in FIG. 8). These artifacts are related to the finite number of encoding steps used by the Fourier transform to reconstruct an image.

It has been verified that Gibbs artifacts increase with an increase in a signal level transition. Coils 100 and 200 each include a common conductor. The common conductor design has significantly higher SNR than previous coil designs. However, these coils also have a much enhanced transition of the signal level in comparison with the current coil design. The presence of these artifacts can be reduced by changing the software and/or hardware of the MR scanner of the MR system. For instance, an enhanced filtering mechanism, such as a low pass filter, can be provided at the scanner to reduce the ripple after a transition from a region of low signal intensity to a region of high signal intensity. In addition, the software of the MR scanner of the MR system could also be reformulated to use a compensation algorithm aimed to cancel out the Gibbs or ringing artifacts. Both of these solutions are undesirable because they require expensive redesigns of the MR scanner. A preferred solution is to reduce the Gibbs artifacts by altering the coil design because the coils are inexpensive, disposable units.

Figure 9:
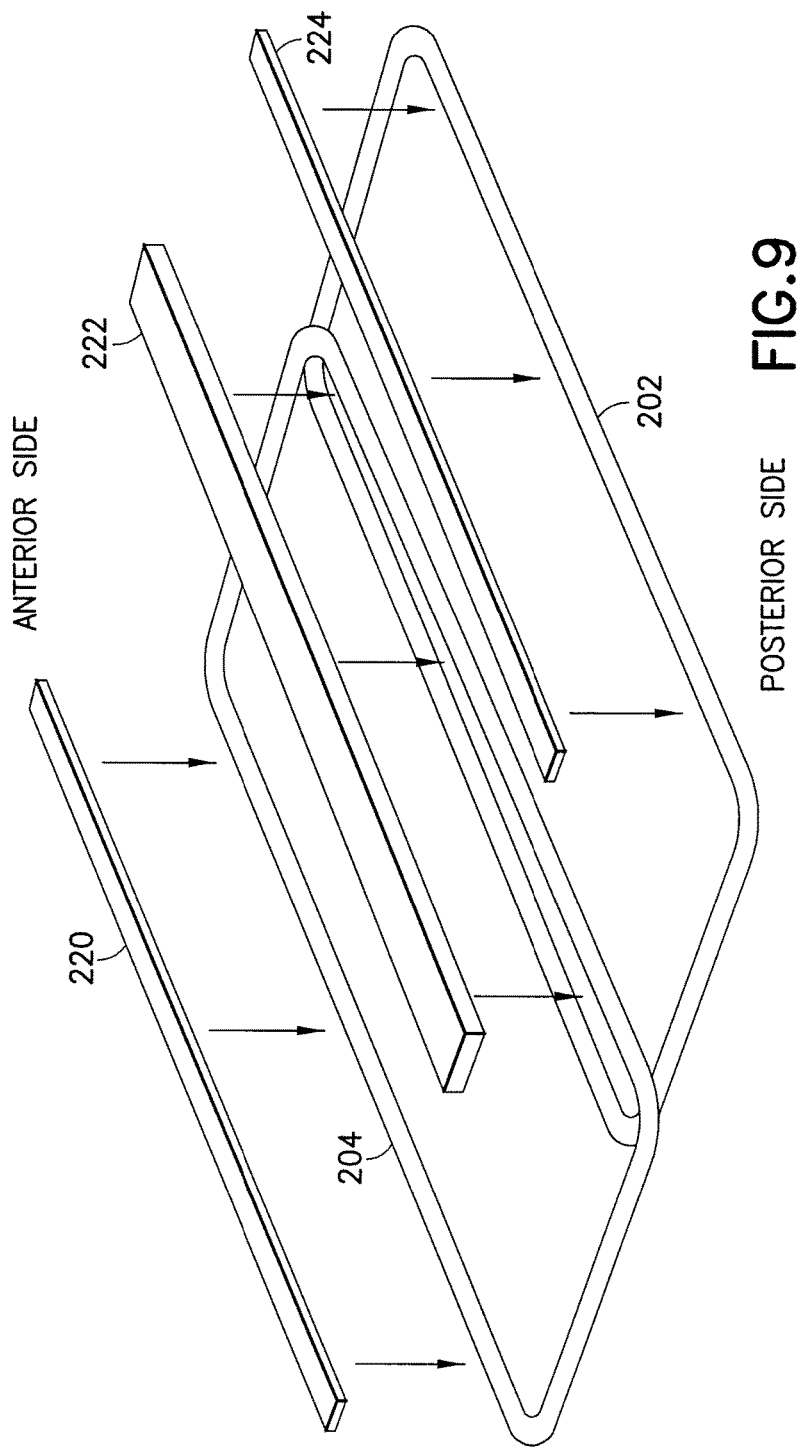
FIG. 9 is a perspective exploded view of a coil in accordance with the present invention illustrating a spacer material used with the coil.
Figure 10:
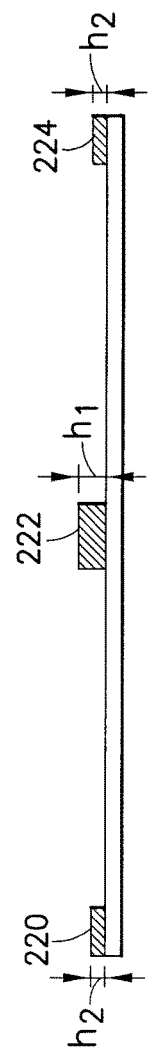
FIG. 10 is a cross-sectional assembled view of the coil of FIG. 9.

Therefore, various tests led to the discovery that changes could be made to the coil and interface device to drastically reduce the presence of Gibbs artifacts. First, it was discovered that spacing the coil away from the surface reduces the transition level. Accordingly and with reference to FIGS. 9 and 10, each of the coil designs discussed herein includes a spacer material positioned adjacent to an anterior surface of the coil. For instance, the spacer material may include three strips 220, 222, and 224. The spacer material strips 220, 222, and 224 have a thickness to assure a predetermined distance of $h_1$ and $h_2$ between the coil and the region of interest, such as a prostate, when the intracavity probe including the coil is inserted into the cavity, such as the rectum, of the patient. The spacer material strip 222 provided over the overlap of the coil loops has a greater thickness than the spacer material strips 220 and 224 at the outside of the coil loops because the artifacts produced in this region are greater than the artifacts produced at the edges. The predetermined distance provided by the spacer material strips is typically about 0.03 inches to about 0.06 inches. The spacer material may be any material that is not detected by an MR system, such as a foam material. While the use of strips of spacer material was described hereinabove, a continuous sheet of spacer material may also be utilized.

By spacing the coil away from the surface, the transition from a region of low signal intensity to a region of high signal intensity is reduced, thereby reducing the Gibbs artifacts. More specifically, the endorectal coil in its current form consists of a pair of coil loops on a substrate, supported by and enclosed in a biocompatible balloon. This balloon is designed to be inflated to press the coil loops against the rectal wall to ensure consistent coil positioning and close contact to enable the best imaging of the prostate gland (in this use case). The fact that the wall thickness of the balloon that covers the coil element is very small (0.010 inches or less) results in close proximity of the coil conductors to the rectal wall.

It is a known phenomenon that an electromagnetic field (and thus the resultant signal intensity as seen by the interface and scanner signal path) follows the "Inverse Square Law," which, applied to this case, means that the signal intensity is inversely proportional to the square of the distance from the coil conductor. In practical terms, it means that a doubling of the distance of the coil conductor from the closest part of patient's anatomy to the coil conductor will result in a signal intensity of $1/4^{th}$ of the previous level in that anatomy, while the reduction in signal will become less apparent further into the region of interest at right angles to the plane of the coil conductors.

Thus, using an arbitrary coil conductor spacing of 0.010 inches, and signal level of 36,000 units (measured as a pixel value of a small region of an imaging phantom representing the patient's anatomy closest to the endorectal coil conductor), doubling the spacing to 0.020 inches, for instance, will result in a reduction of signal intensity in the same region to 9,000 units. Hence, a pre-determined spacing provided on top of the coil conductor reduces the signal intensity jump at the proximal region of the imaging volume, and thus works favorably to reduce the artifacts including Gibbs artifacts.

In addition, it was discovered that the signal could be reduced accompanied by a greater reduction in the noise to increase the SNR while reducing artifacts by making minor changes in the interface device. First, the interface device includes a pair of preamplifiers as will be discussed in greater detail hereinafter. It has been found that providing the preamplifiers with a predetermined reduced supply voltage as compared to a rated supply voltage of the preamplifiers has the effect of reducing the signal produced by the coil; however, this reduction in signal is accompanied by a greater reduction in noise. Accordingly, the SNR is increased. For example, these preamplifiers are typically provided with a supply voltage of 10V. It has been found that decreasing the supply voltage of the preamplifier to 5V, and the positioning of an attenuator having an attenuation of between 3 dB and 9 dB after the preamplifiers, has the effect of reducing the signal produced by the coil. This reduction in signal, however, is accompanied by a greater reduction in noise. Accordingly, the SNR is increased.

Finally, while the combination of spacing the coil away from the surface and applying the preamplifier with a reduced supply voltage of 5V lowers the Gibbs artifacts produced in the images significantly, the artifacts produced in the images are still greater than in current coil designs. Accordingly, it was discovered that reduced signal intensity associated with reduced artifacts without compromising on SNR could be achieved by utilizing a coil having an overlapped two loop design where the two loops do not include a common conductor or a common ground.

Figure 11:
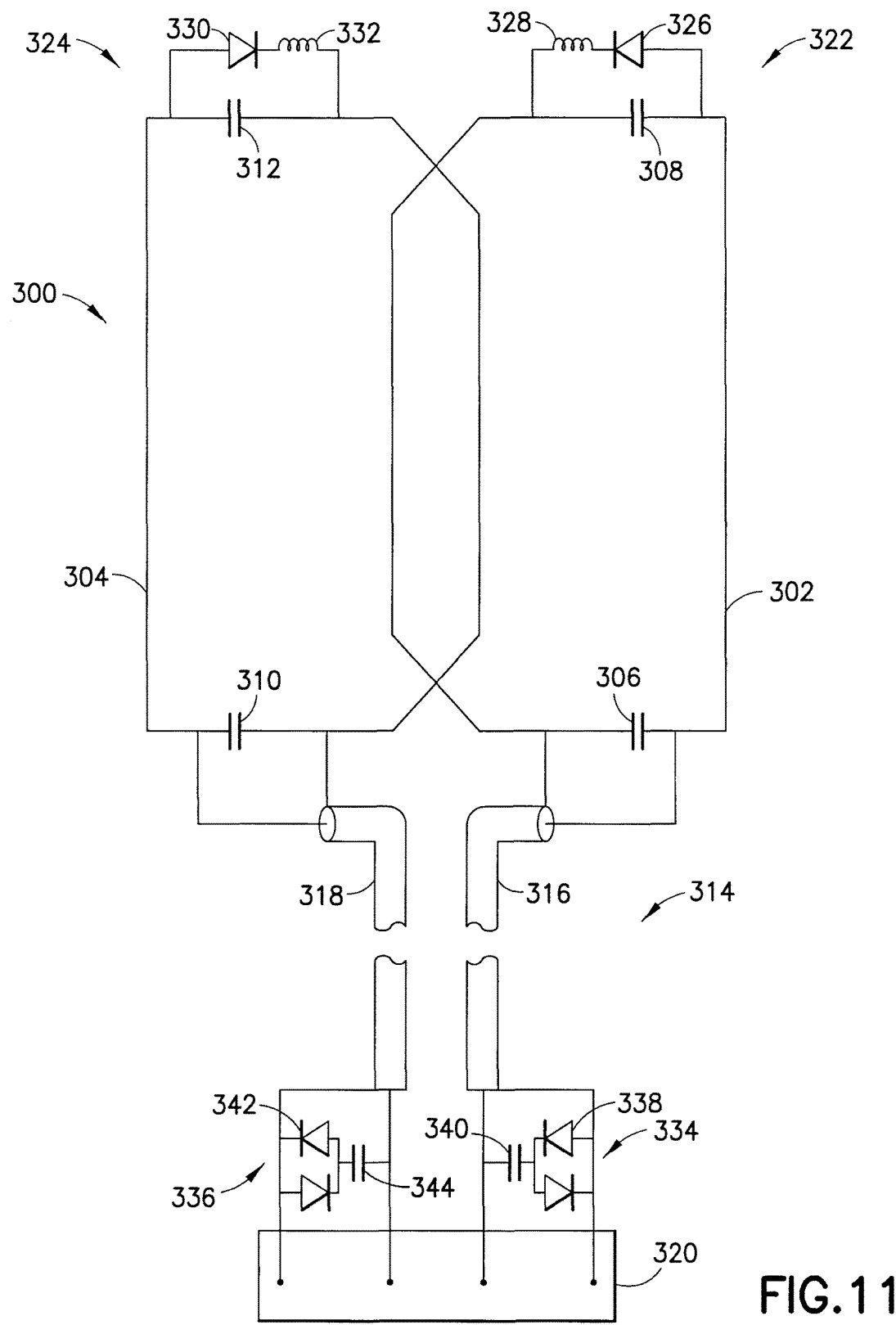
FIG. 11 is a schematic diagram of a coil in accordance with a third embodiment of the present invention.

More specifically, with reference to FIG. 11, a third embodiment of the endorectal coil, generally designated as 300, includes a first coil loop 302 and a second coil loop 304. The pair of coil loops 302 and 304 is arranged in a phased array configuration each of which receive MR signals from the region of interest corresponding thereto. The first coil loop 302 includes a drive capacitor 306 and a tuning capacitor 308. The tuning capacitor 308 has a value selected to resonate the first coil loop 302 at the operating frequency of the MR system. The second coil loop 304 includes a drive capacitor 310 and a tuning capacitor 312. The tuning capacitor 312 has a value selected to resonate the second coil loop 304 at the operating frequency of the MR system.

The coil 300 also includes an output line 314 that includes two coaxial cables 316 and 318. The first coaxial cable 316 is connected at a first end thereof across the first drive capacitor 306 and the second coaxial cable 318 is connected at a first end thereof across the second drive capacitor 310 such that each of the drive capacitors 306 and 310 is provided with a separate ground.

Accordingly, the third embodiment of coil 300 also includes two elements (i.e., first coil loop 302 and second coil loop 304) and is configured to provide a four channel output. More specifically, coil 300 is configured to provide a first channel output representative of the whole loop, and a second channel output representative of the saddle/butterfly mode. In addition, based on an RF splitter configuration of the interface device discussed hereinafter, a third channel output may be provided to obtain a left loop signal and a fourth channel output may be provided to obtain a right loop signal.

A standard plug 320 accommodates the conductors of both cables at a second end thereof, for instance, the center and shield conductors of each cable 316 and 318 such that the output line 314 can be connected to a suitable socket or other type of connector for the interface device.

It was also discovered that the previously described embodiments of the coil were not designed to operate within safe SAR limits. Accordingly, additional decoupling circuitry is required to achieve these safe SAR limits More specifically, a first active decoupling circuit 322 is connected across the tuning capacitor 308 of the first coil loop 302, and a second active decoupling circuit 324 is connected across the tuning capacitor 312 of the second coil loop 304. Each of these decoupling circuits 322, 324 include a PIN diode 326, 330 and an inductor 328, 332 provided in series. During the transmit cycle, the interface device is configured to bias the PIN diodes 326, 330 on, thereby opening the coil due to the parallel resonance. In addition, a first passive decoupling circuit 334 is provided at the second end of the first coaxial cable 316, and a second passive decoupling circuit 336 is provided at the second end of the second coaxial cable 318. Each of these passive decoupling circuits 334, 336 includes series connected back-to-back diodes 338, 342 and a capacitor 340, 344. The passive decoupling circuits 334, 336 are configured to conduct in response to the higher voltages induced by the RF excitation field. The use of these passive decoupling circuits 334, 336 removes the necessity for the output line 314 to have an electrical length of $S_L+n(\lambda/4)$. Accordingly, the output line 314 may have any practical electrical length.

Figure 12:
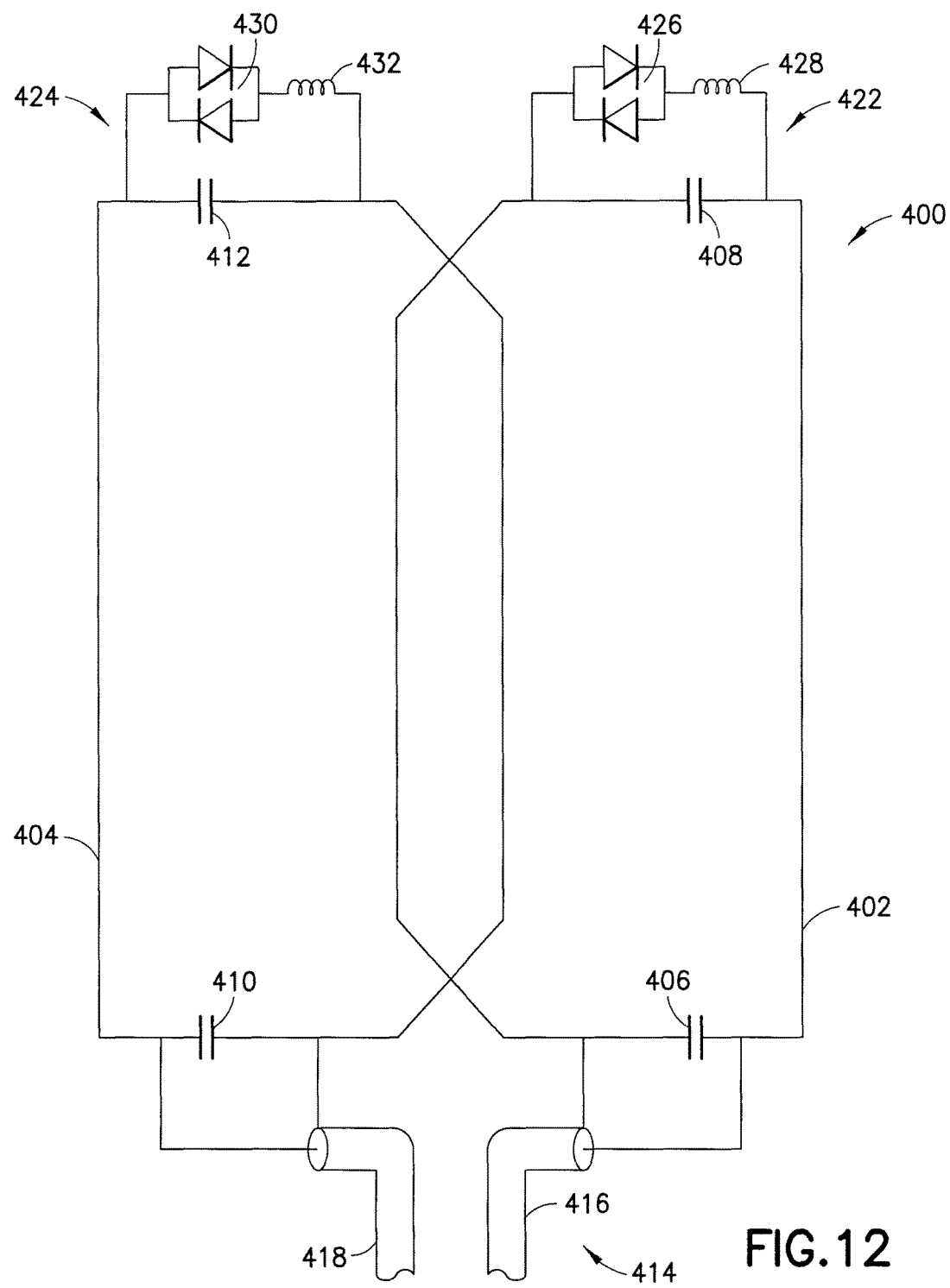
FIG. 12 is a schematic diagram of a coil in accordance with a fourth embodiment of the present invention.

An alternative configuration of the endorectal coil in accordance with a fourth embodiment of the present invention is illustrated in FIGS. 12, 13A, and 13B. The endorectal coil, generally designated as 400, includes a first coil loop 402 and a second coil loop 404. The pair of coil loops 402 and 404 is arranged in a phased array configuration, each of which receive MR signals from the region of interest corresponding thereto. The first coil loop 402 includes a drive capacitor 406 and a tuning capacitor 408. The tuning capacitor 408 has a value selected to resonate the first coil loop 402 at the operating frequency of the MR system. The second coil loop 404 includes a drive capacitor 410 and a tuning capacitor 412. The tuning capacitor 412 has a value selected to resonate the second coil loop 404 at the operating frequency of the MR system.

The coil 400 also includes an output line 414 that includes two coaxial cables 416 and 418. The first coaxial cable 416 is connected at a first end thereof across the first drive capacitor 406, and the second coaxial cable 418 is connected at a first end thereof across the second drive capacitor 410 such that each of the drive capacitors 406 and 410 is provided with a separate ground.

Accordingly, the fourth embodiment of coil 400 also includes two elements (i.e., first coil loop 402 and second coil loop 404) and is configured to provide a four channel output. More specifically, coil 400 is configured to provide a first channel output representative of the whole loop, and a second channel output representative of the saddle/butterfly mode. In addition, based on an RF splitter configuration of the interface device discussed hereinafter, a third channel output may be provided to obtain a left loop signal and a fourth channel output may be provided to obtain a right loop signal. Each of these modes is discussed in greater detail hereinafter with reference to FIGS. 15-22.

The coil 400 also includes a first passive decoupling circuit 422 connected across the tuning capacitor 408 of the first coil loop 402, and a second passive decoupling circuit 424 connected across the tuning capacitor 412 of the second coil loop 404. Each of these decoupling circuits 422, 424 includes series connected back-to-back diodes 426, 430 and an inductor 428, 432. The passive decoupling circuits 422, 424 are configured to conduct in response to the higher voltages induced by the RF excitation field. Accordingly, the passive decoupling circuits 422, 424 cause the coil to function as an open circuit during the RF transmit cycle. It should be noted that the diode combinations of the passive decoupling circuits 422, 424 could also provide the functionality of an active decoupling diode. Accordingly, although FIG. 12 only shows a pair of passive decoupling circuits 422, 424, it should be apparent to one skilled in the art that these passive decoupling circuits 422, 424 could be configured as both passive and active decoupling circuits.

With specific reference to FIGS. 13A and 13B and continued reference to FIG. 12, a standard plug 434 accommodates the conductors of both cables 416 and 418 of output line 414 at a second end thereof, for instance, the center and shield conductors of each cable 416 and 418. The output line 414 may also be provided with a handle 436 to allow for easier handling of the intracavity probe. The requirement of the output line 414 having an electrical length of $S_L+n(\lambda/4)$ is eliminated in this embodiment with the addition of an intermediate conduit 438. The intermediate conduit 438 has an input connector 440 corresponding to and for connection with the plug 434 of the output line 414, and an output connector 442 for connection to an interface device 500. The intermediate conduit 438 also includes a pair of internal cables for connecting at one end thereof, respectively, to the coaxial cables 416 and 418 of the intracavity probe via the input connector 440 and approximate another end thereof to the interface device 500 via the output connector 442. A pair of baluns 444 is also provided. Each of the baluns 444 is interconnected between an end of one of the internal cables and the input connector 440. It should also be noted that the pair of baluns 444 could also be connected between the end of one of the internal cables and the output connector 442 at both the output and input ends of the intermediate conduit 438. The intermediate conduit 438 further includes at least one cable trap 446, and desirably two cable traps 446 as shown in FIG. 13B, connected thereabout. The cable traps 446 prevent undesired current from flowing on the shield conductors of the pair of internal cables of the intermediate conduits. The interface device 500 is connected to the MR system via a cable 448 and a connector 450. The cable 448 may have a cable trap 452 positioned thereabout.

Due to the desire for a small, flexible, damage-resistant intracavity probe, whose design minimizes the likelihood of any internal componentry protruding through the balloon-type enclosure in which it is housed, each of the coils discussed hereinabove may be constructed of a thin, flexible dielectric material with copper patterns applied to both sides to form not only the conductive pathways but also all of the capacitors required for tuning and decoupling. Moreover, as each of the coils is intended to be offered as an integral part of a one-use disposable intracavity probe, such a fabrication technique will aid in the goal of realizing substantial savings during the manufacture of the probes. This is because the fabrication process for "preprinted" coils will involve significantly less labor and less time to inspect the finished product as compared to coils made from discrete components.

The most effective passive decoupling scheme for the 2-loop endorectal coil disclosed herein is to use a non-magnetic, pre-packaged set of 4 anti-parallel silicon PIN diodes in series with the appropriate inductor to affect a blocking impedance across each loop's tuning capacitor as shown in FIG. 12. However, this is a very expensive solution for the endorectal coil, as it is intended to be a "single use" device, to be disposed of after a single scan procedure.

In an effort to provide a safe, yet cost effective method of passive decoupling, an alternate method was employed for the endorectal coil as shown in FIG. 11. Passive decoupling circuits 334, 336 comprising a chip capacitor in series with an inexpensive anti-parallel signal diode (in this case, for example, the part was a BAV-99) are connected between the center conductor and shield of each of the coil's coaxial cables, on a small PCB that also mounts the coil's RF plug 320. The value of the chip capacitor was chosen so that in combination with the coaxial cable stub length of 8.5 inches (24 degrees at 64 MHz), an inductive reactance equal to the capacitive reactance of the loop's drive capacitor would result in a parallel-resonant blocking circuit in the coil loop upon diode conduction.

If the unlikely condition occurs that a patient is scanned using the endorectal coil without its dedicated interface device (which provides coil-type detection and active decoupling bias circuitry), the coil loops will couple to the scanner's body transmit coil and generate a small RF voltage which will propagate from the coil elements to the signal diodes through the coaxial cable and chip capacitor. As this voltage rises above the conduction threshold of the diode pair, they will start to conduct, thus acting like a resistor in series with the capacitor. This results in the blocking impedance increasing across the loop's drive capacitor, and as a consequence, the loop current will be diminished. It can be deduced that if incrementally more RF power is applied to the loop, that power will serve to cause the diodes to conduct further, until they reach full conduction. At this "equilibrium" point, the loop serves as a voltage source, and most of the absorbed power is distributed between the loop's drive capacitor, the coaxial cable (which serves as a lossy inductance), the decoupling chip capacitor, and the diode pair.

Careful testing and implementation of this method is required using temperature testing of the various components and the coil loop itself to ensure that the equilibrium point does not result in any excessive component heating or excess SAR generated by the coil loop. In any event, this method serves as a "second fault" safety measure, and is anticipated to be a rare occurrence.

This method also confers a cost advantage in that the diode pair and the decoupling capacitor are located far enough from the imaging region of interest that commercial components with slightly magnetic properties are acceptable for use. Accordingly, the coil configuration illustrated in FIG. 11 is the presently preferred embodiment.

Figure 14:
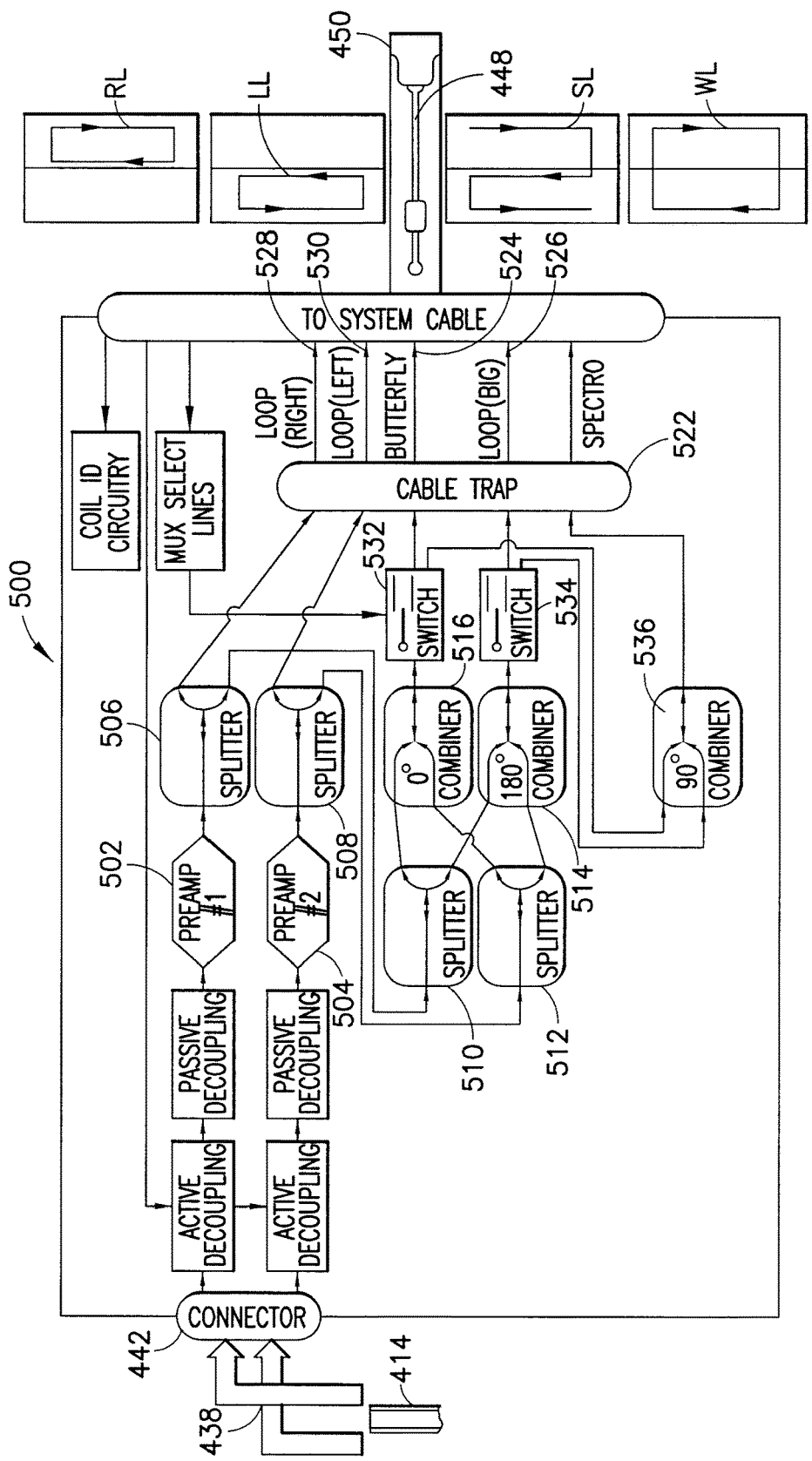
FIG. 14 is a block diagram of an interface device in accordance with the present invention.

With reference to FIG. 14 and with continuing reference to FIGS. 12, 13A, and 13B, an embodiment of an interface device, generally denoted as reference numeral 500, for interfacing the coil 400 with the appropriate input port(s) of a 1.5 T MR system is illustrated.

The interface device 500 includes preamplifier networks 502 and 504, power splitter networks 506, 508, 510, and 512, a 180 degree combining network 514, and a zero degree combining network 516. Attenuators (not shown) are provided to nominally attenuate the signal from about 3 dB to about 9 dB. The attenuators may be positioned at at least one of the following locations: (a) between the first preamplifier network 502 and the first power splitter network 506; (b) between the second preamplifier network 504 and the second power splitter network 508; (c) after the first power splitter network 506; and (d) after the second power splitter network 508. The power splitter and combining networks may be implemented with standard Wilkinson style designs, and the preamplifier networks may ideally be realized with 28 dB nominal gain. The preamplifier networks 502 and 504 may be implemented using commercially available miniature low-noise, 28 dB gain shielded units with a tuned input circuit designed to present a low impedance (Ω real) at the Larmor frequency. Close proximity of the preamplifier networks 502 and 504 to their respective PIN diodes 518, 520 (see FIG. 16) in view of the low impedance of the former allows some measure of isolation during the receive cycle from other surface coils (or arrays of same) used in conjunction with the coil 400. Passive protection diode networks are included in interface device 500 to prevent excessive RF voltage from damaging the preamplifier networks 502 and 504 during the RF transmit pulse should interface device 500 be disconnected while inside the bore of the MR system during the transmit cycle. These diode networks also provide some decoupling for the coil in the same scenario.

The power splitter networks 506 and 508 are used as 50 ohm/0 degree splitters at the outputs of the preamplifier networks 502 and 504. The power splitter networks 510 and 512 are also used as 50 ohm/0 degree splitters at one output of each of the power splitter networks 506 and 508. The other output of each of the power splitter networks 506 and 508 is sent directly to a cable trap 522 which directs the output to one of four channels 524, 526, 528, and 530. The two combining networks 514 and 516 are also configured as 50 ohm devices. As a result, these four networks may be interconnected as shown by means of four equal-phase length 50 ohm coaxial cable, PCB stripline, microstrip, or other transmission line media. In addition, the output of the two combining networks 514 and 516 is provided to a pair of switching networks 532 and 534 which directs the signal to the appropriate channel or, optionally, to a 90 degree hybrid combining network 536 if the scanner or MR system is configured to operate in a spectroscopic mode.

As should be apparent based on the above description of the present invention, the endorectal coils disclosed herein include a two element layout that has been configured to receive radio frequency (RF) currents from the whole geometry and, using appropriate splitters and combiners in the interface device, turned into a four channel output device. More specifically, the two element common conductor layout disclosed herein can produce two loops or a loop and saddle combination based on the combiner networks from the same feedpoints. In addition, both of these unique field patterns can be obtained separately such that four (4) unique channels which have unique radiation patterns associated with the RF current distribution can be obtained. It is apparent to one of ordinary skill in the art that one can extend this by creating various other phase combination networks and get useful signal in addition to the above mentioned as well. There are numerous possibilities to get various different field patterns based on the splitter-combiner networks and achieve more than 2 (3, 4, 6, 8, etc.) individual channel outputs. It is also possible to extend this theory to more than two elements and achieve the same advantage of increased channel output, which has been demonstrated to yield superior SNR than merely the two element contribution.

It is also apparent, given the greater number of receivers available in current MR scanners, that coil layouts having a smaller number of imaging elements can be built with the disclosed technology to take advantage of those fewer imaging elements to create imaging systems having a greater number of channels, thereby leading to lower costs. For example, a current 16 element coil layout utilizes 16 preamplifiers in the interface device even for an 8 channel multiplexed or combined output. By utilizing the theory of the present invention, a coil having a 16 element coil element involves utilizing only 8 preamplifiers to obtain a 16 channel output. This would significantly contribute to less complex circuitry because half the number of preamplifiers and associated circuitry are required; better cable management because half the number of RF cables are required to be managed; less expensive to make; easier to fabricate and tune, yet with maximized performance for the region of interest selected. In addition, such coil layouts provide increased depth of penetration over current coils because it is well known in the art that larger loops lead to a greater depth of penetration.

Having set forth the components of the present invention, the operation of coil 400 and interface device 500 in various modes will be discussed hereinafter with reference to FIGS. 13-19. Although the following description is based on the coil 400 illustrated in FIG. 12, this description is equally applicable to the embodiments of the coil illustrated in FIGS. 6, 7, and 11 as well.

Left Loop Mode

With reference to FIGS. 15 and 16A-16C, the operation of coil 400 and interface device 500 when in Left Loop mode will now be described. During transmit mode, PIN diode 518 is turned on by a signal from a PIN diode bias 538 (see FIG. 16C). This PIN diode 518 provides an RF short circuit to ground, which is reflected as an open circuit at coaxial cable 416. Accordingly, first coil loop 402 is isolated and shown in phantom in FIG. 15.

Figure 15:
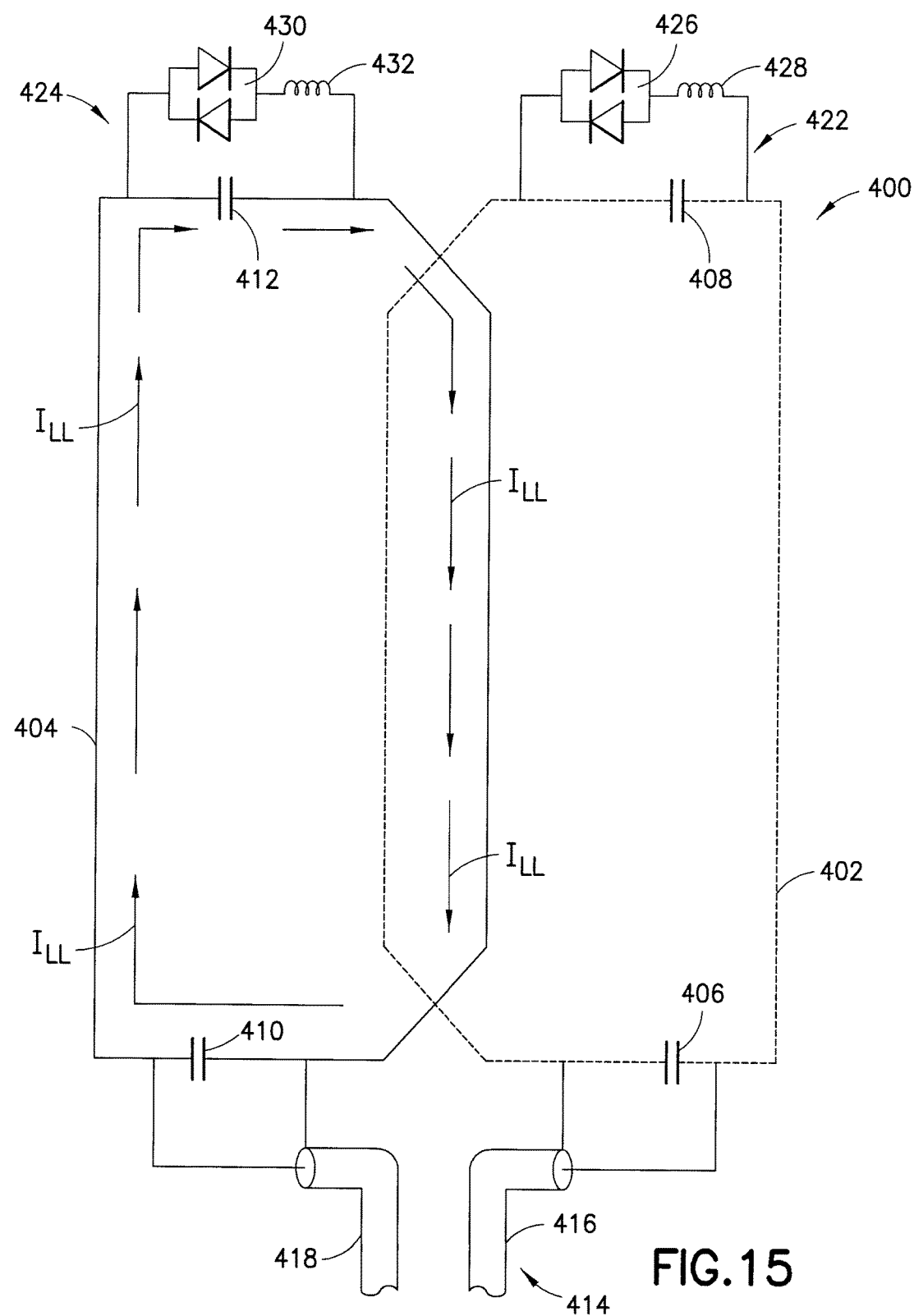
FIG. 15 is a schematic diagram of the coil of FIG. 12 illustrating the manner in which current is induced therein when in Left Loop mode.

As shown in FIG. 15, during the receive cycle, current will only be seen as flowing through the second coil loop 404 due to the PIN diode 518 acting as an RF "open" to help in isolating the first coil loop 402. Accordingly, current flows in the second coil loop 404 as shown by arrow $I_{LL}$, as shown in FIG. 15.

Figures 16, 16A:
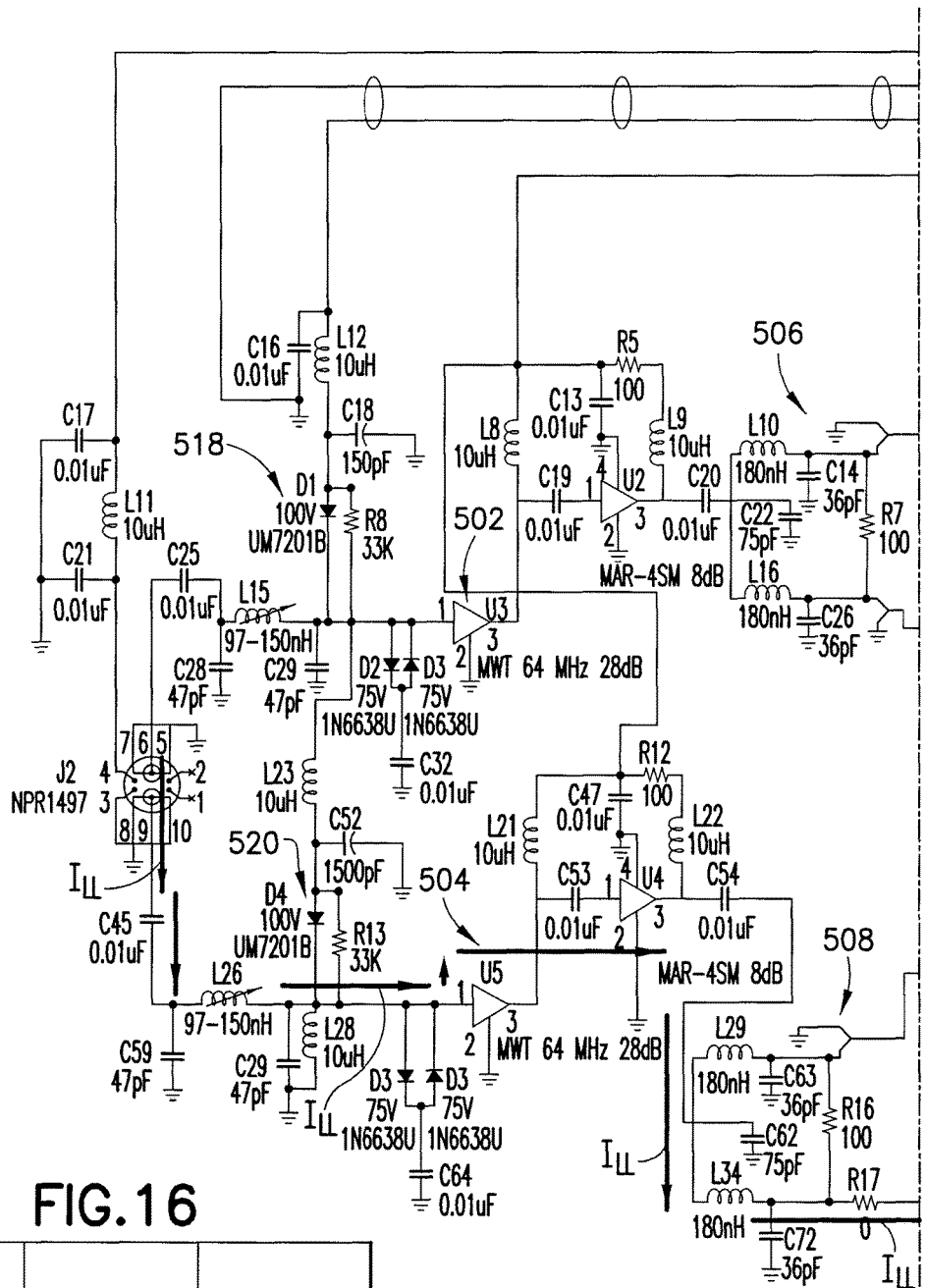
FIG. 16 is made up of FIGS. 16A, 16B, and 16C.
FIGS. 16A-16C form a schematic diagram of the interface device of FIG. 14 illustrating the manner in which the interface device operates when in Left Loop mode.
Figure 16B:
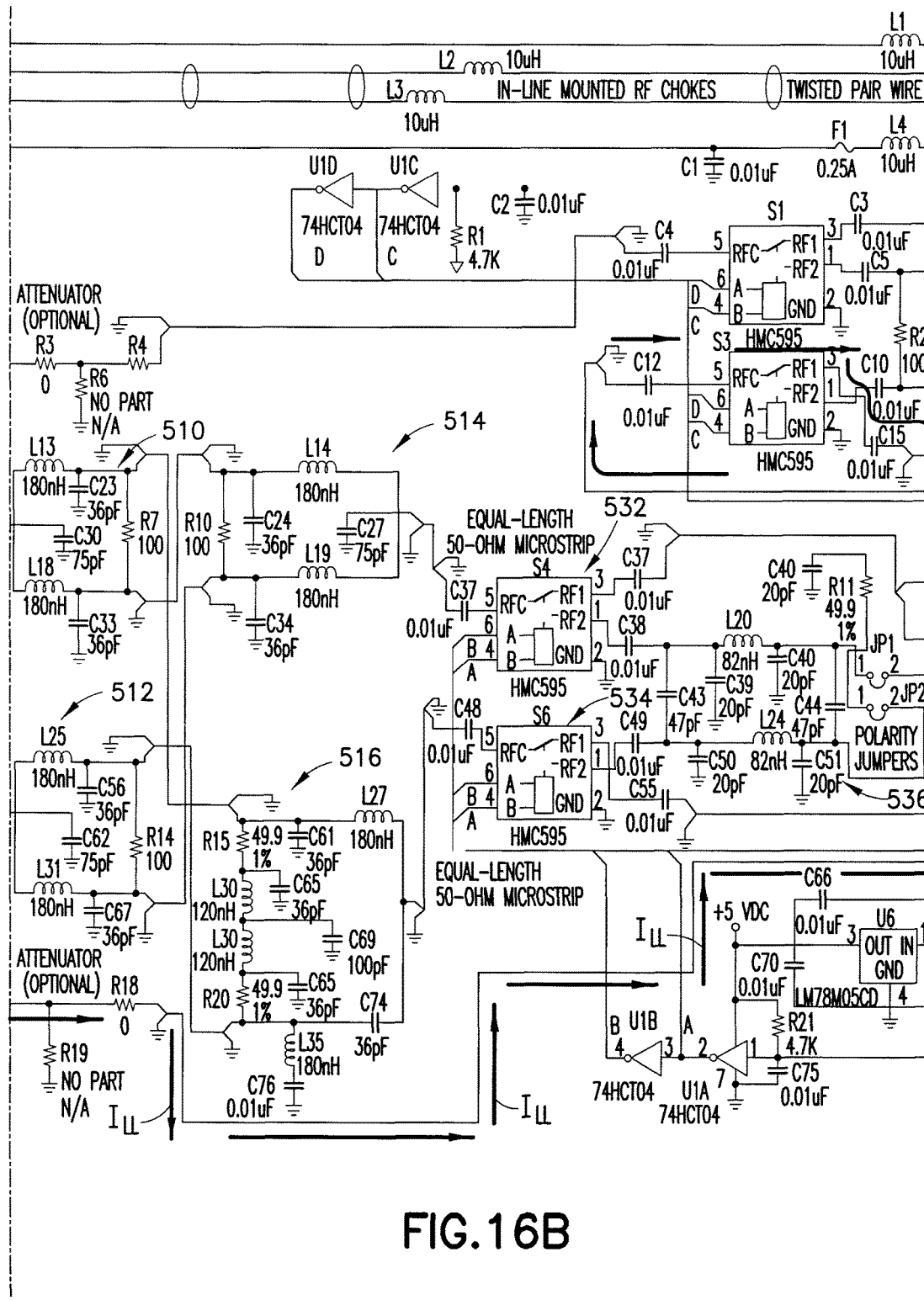
Figure 16C:
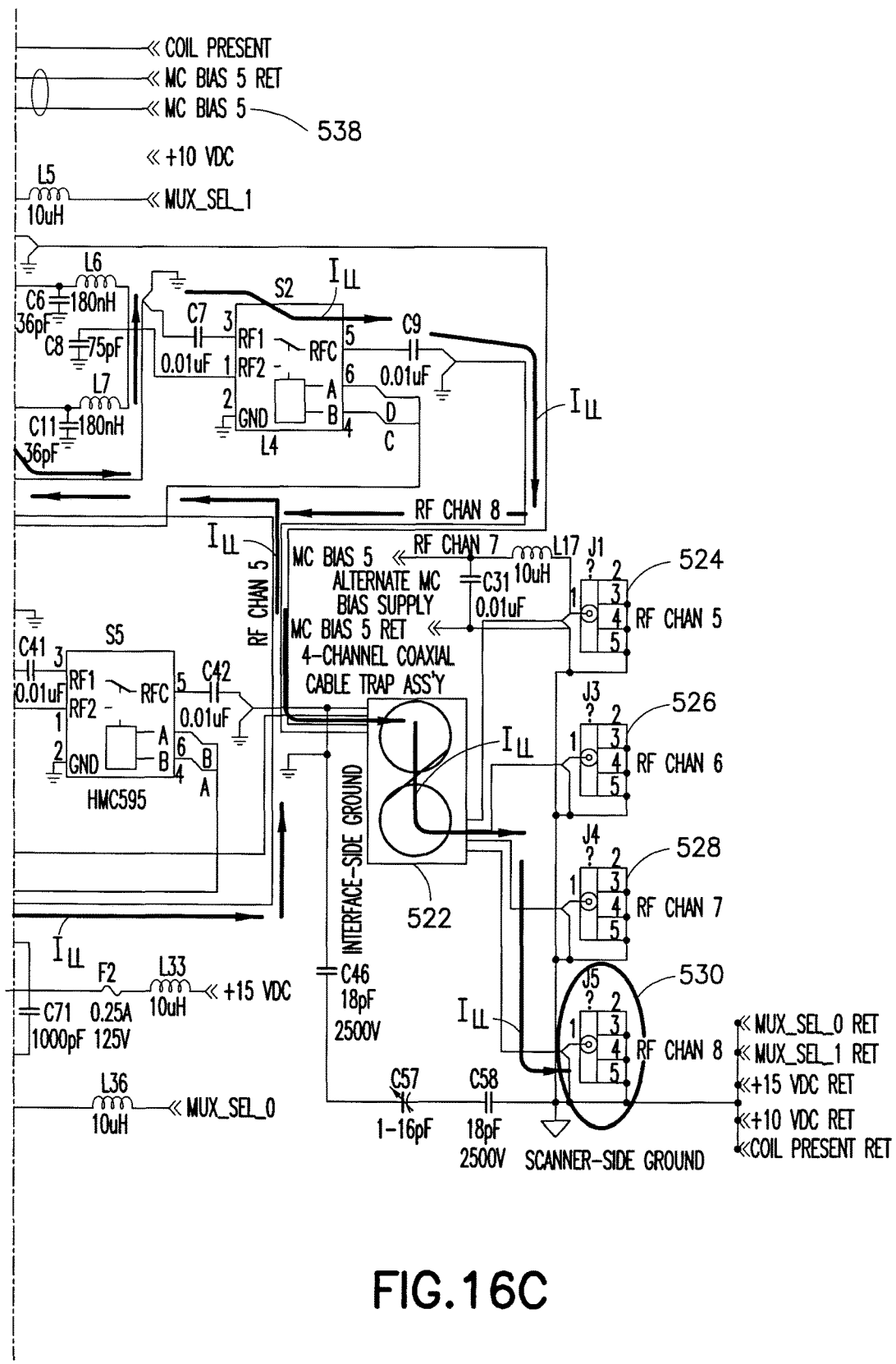

With reference to FIGS. 16A-16C, the manner in which interface device 500 processes the voltage signals received from coaxial cable 418 is now described. The signal from the drive capacitor 410 is first sent through preamplifier network 504, which amplifies the voltage signal and passes the resulting amplified version to power splitter network 508. One of the outputs of the power splitter 508 is provided to a second power splitter network 512 and the other output is sent to the cable trap 522. The cable trap 522 sends this signal to the fourth output channel 530 representing the left loop signal.

The flow of current through interface device 500 when in Left Loop mode is shown by arrow $I_{LL}$ in FIGS. 16A-16C.

Right Loop Mode

With reference to FIGS. 17 and 18A-18C, the operation of coil 400 and interface device 500 when in Right Loop mode will now be described. During transmit mode, PIN diode 520 is turned on by a signal from a PIN diode bias 538 (see FIG. 18C). This PIN diode 520 provides an RF short circuit to ground, which is reflected as an open circuit at coaxial cable 418. Accordingly, second coil loop 404 is isolated and shown in phantom in FIG. 17.

Figure 17:
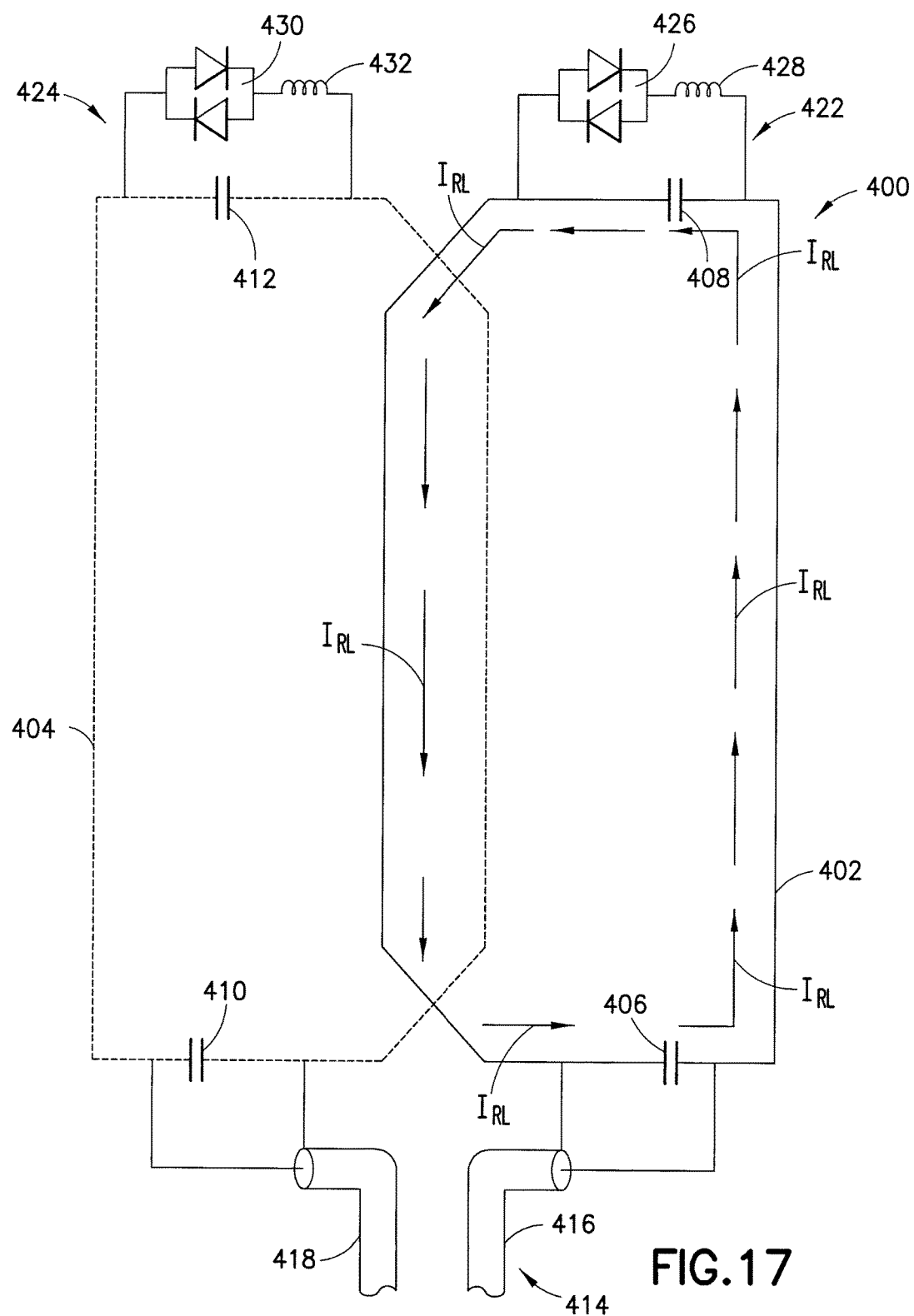
FIG. 17 is a schematic diagram of the coil of FIG. 12 illustrating the manner in which current is induced therein when in Right Loop mode.

As shown in FIG. 17, during the receive cycle, current will only be seen as flowing through the first coil loop 402 due to the PIN diode 520 acting as an RF "open" to help in isolating the second coil loop 404. Accordingly, current flows in the first coil loop 402 as shown by arrow $I_{RL}$, as shown in FIG. 17.

Figures 18, 18A:
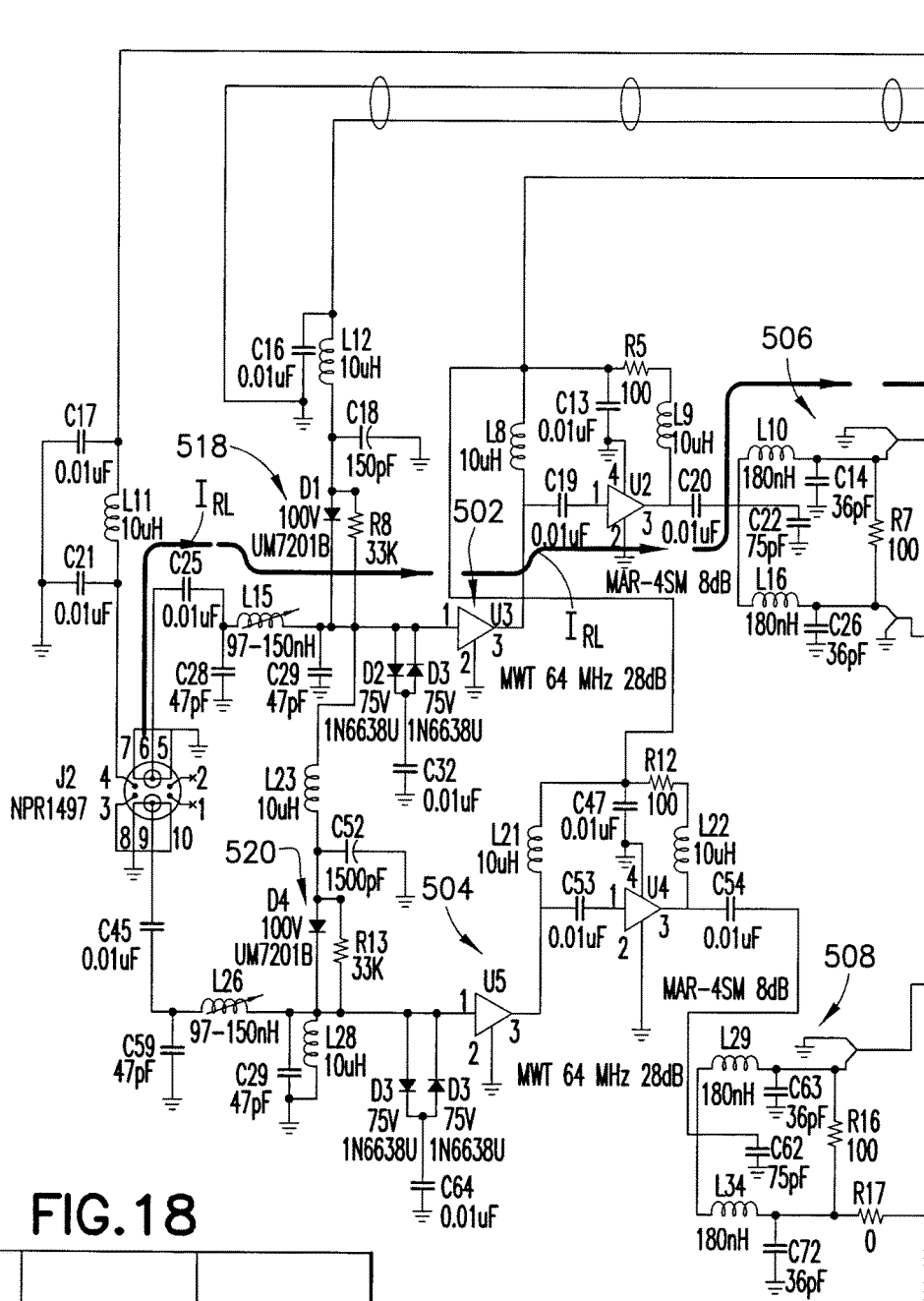
FIG. 18 is made up of FIGS. 18A, 18B, and 18C.
FIGS. 18A-18C form a schematic diagram of the interface device of FIG. 14 illustrating the manner in which the interface device operates when in Right Loop mode.
Figure 18B:
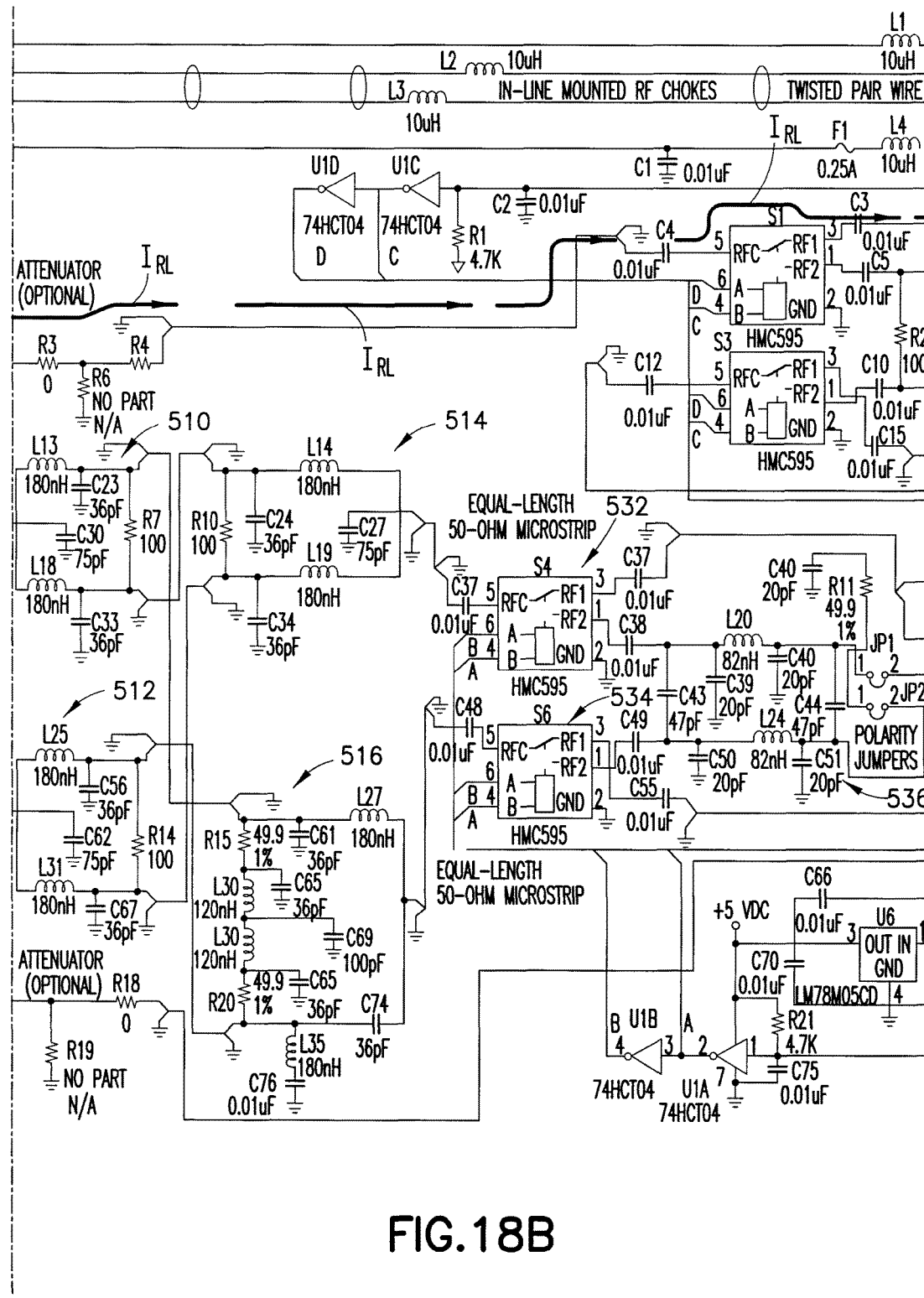
Figure 18C:
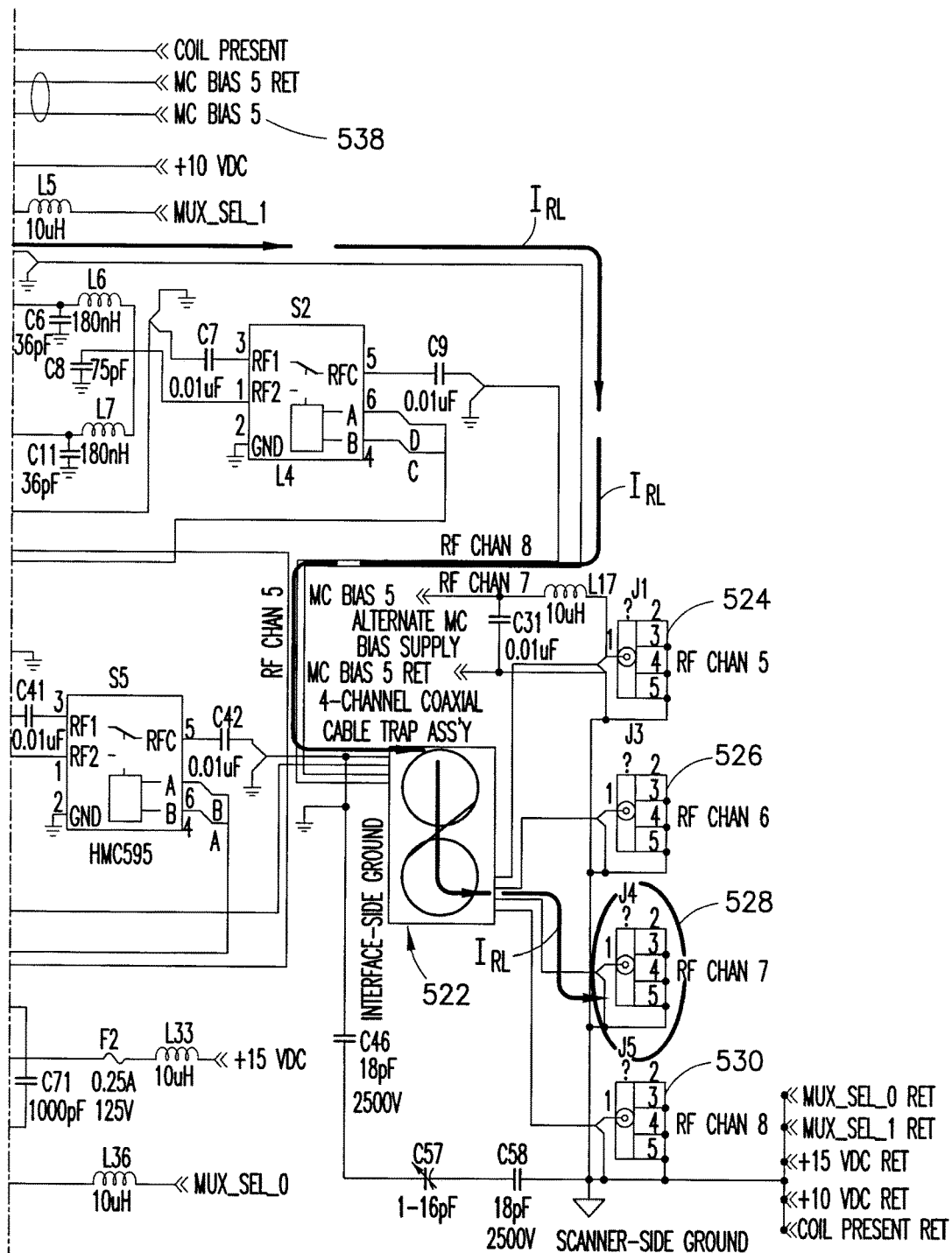

With reference to FIGS. 18A-18C, the manner in which interface device 500 processes the voltage signals received from coaxial cable 416 is now described. The signal from the drive capacitor 406 is first sent through preamplifier network 502, which amplifies the voltage signal and passes the resulting amplified version to power splitter network 506. One of the outputs of the power splitter 506 is provided to a second power splitter network 510 and the other output is sent to the cable trap 522. The cable trap 522 sends this signal to the third output channel 528 representing the right loop signal.

The flow of current through interface device 500 when in Right Loop mode is shown by arrow $I_{RL}$ in FIGS. 18A-18C.

Right Loop and Left Loop or LL Mode

The operation of coil 400 and interface device 500 when in LL mode, will now be described. During the receive cycle, when operating in LL mode, coil 400 operates in the same manner as described hereinabove for both the Right Loop and Left Loop modes. However, interface device 500 functions in a slightly different manner Instead of turning on one of PIN diodes 518 and 520 by a signal from a PIN diode bias 538, both of these PIN diodes 518 and 520 remain off such that both a Right Loop signal and Left Loop signal, as described hereinabove, are provided to the third output channel 528 and the fourth output channel 530, respectively. Accordingly, a 2-channel signal is provided to the host scanner.

Whole Loop Mode

With reference to FIGS. 19 and 20A-20C, during the receive cycle, the current induced by the vertically oriented MR signals within an outer loop of coil 400 can be represented by $I_{WL}$, as it is the signal current shown flowing into and out of the loop.

Figure 19:
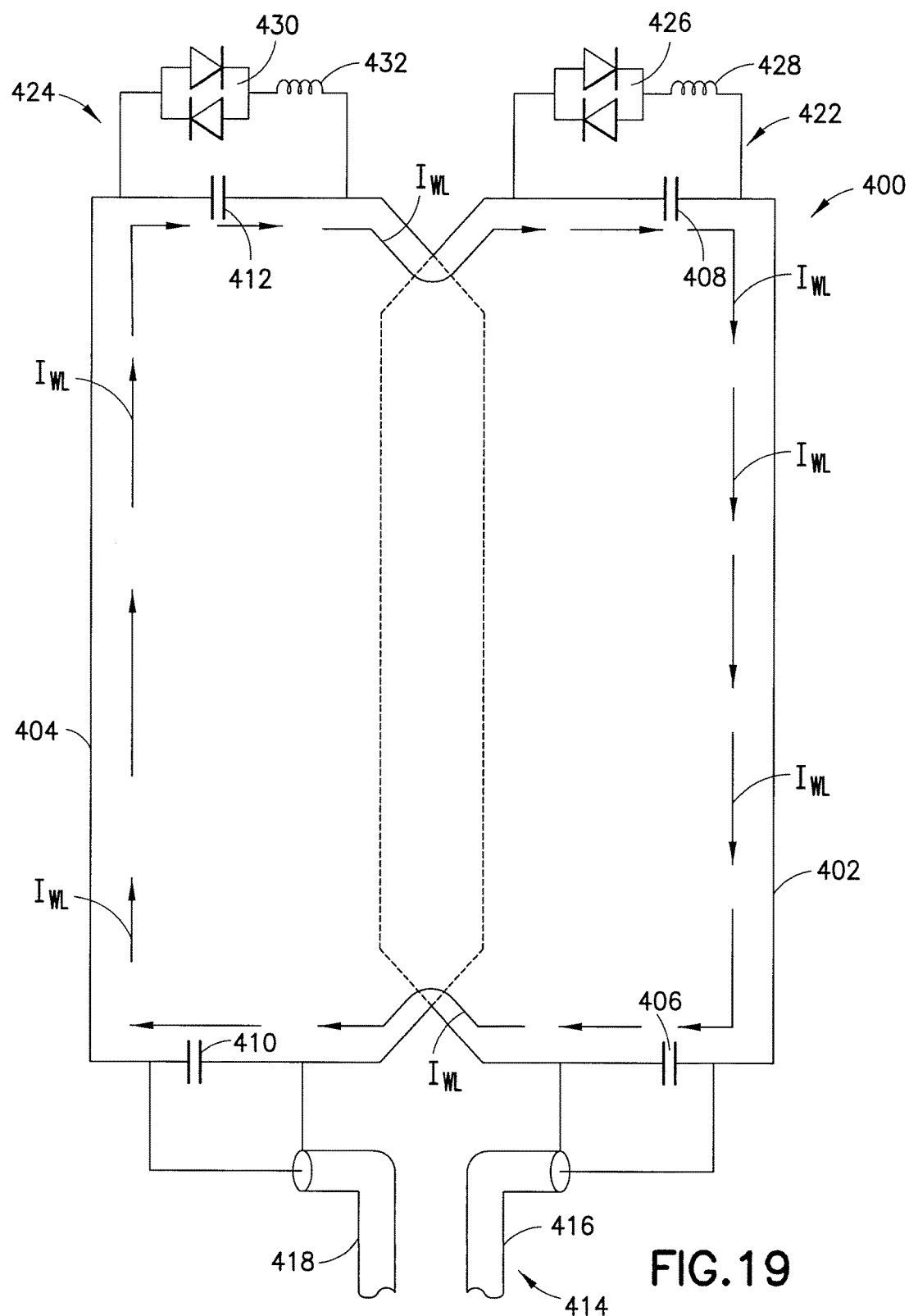
FIG. 19 is a schematic diagram of the coil of FIG. 12 illustrating the manner in which current is induced therein when in Whole Loop mode.

In this configuration, as the current $I_{WL}$ flows through the first coil loop 402 and the second coil loop 404, no current is seen flowing through the right edge of the second coil loop 404 and the left edge of the first coil loop 402. Accordingly, the right edge of the second coil loop 404 and the left edge of the first coil loop 402 act as an open circuit relative to the current flowing in the outer loop shown by arrows $I_{WL}$. Therefore, the right edge of the second coil loop 404 and the left edge of the first coil loop 402 are illustrated in FIG. 19 in phantom.

Having completed discussion of the manner in which current flows through coil 400 during a receive cycle when in Whole Loop mode, a description of the operation of interface device 500 during the receive cycle of the MR system when in Whole Loop mode will now be described with specific reference to FIGS. 20A-20C. Coil 400 outputs voltage signals representative of MR signals of both horizontal and vertical orientation. For ease of description, the voltage signals representative of the MR signals of horizontal orientation are referred to herein as "0 degree horizontal voltage signals" because they have the same phase at each port. The voltage signals representative of the MR signals of vertical orientation are referred to as "0 degree vertical voltage signals" for those output across the drive capacitor 406 of the first coil loop 402, and "180 degree vertical voltage signals" for those output from the drive capacitor 410 of the second coil loop 404.

Figures 20, 20A:
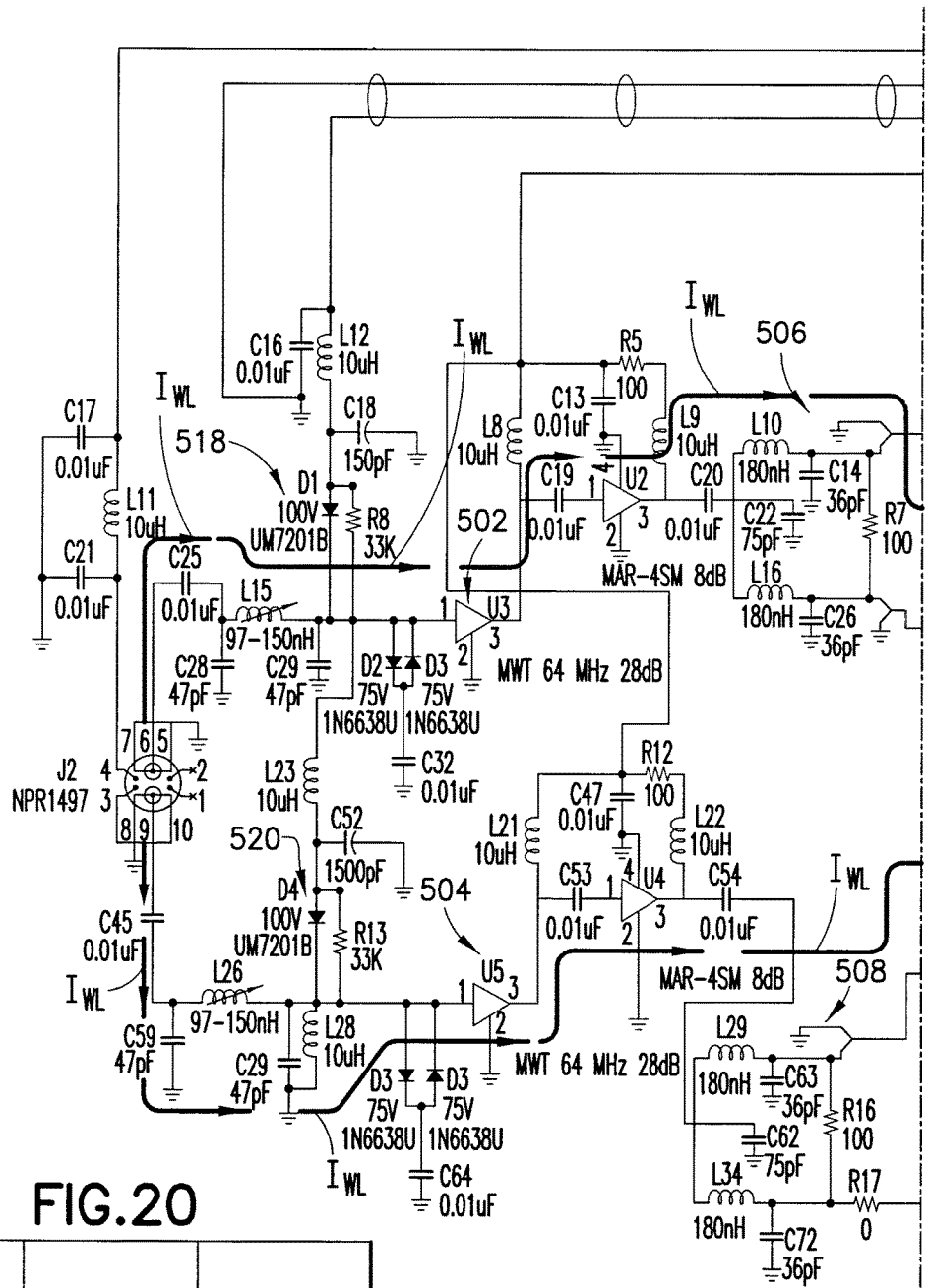
FIG. 20 is made up of FIGS. 20A, 20B, and 20C.
FIGS. 20A-20C form a schematic diagram of the interface device of FIG. 14 illustrating the manner in which the interface device operates when in Whole Loop mode.
Figure 20B:
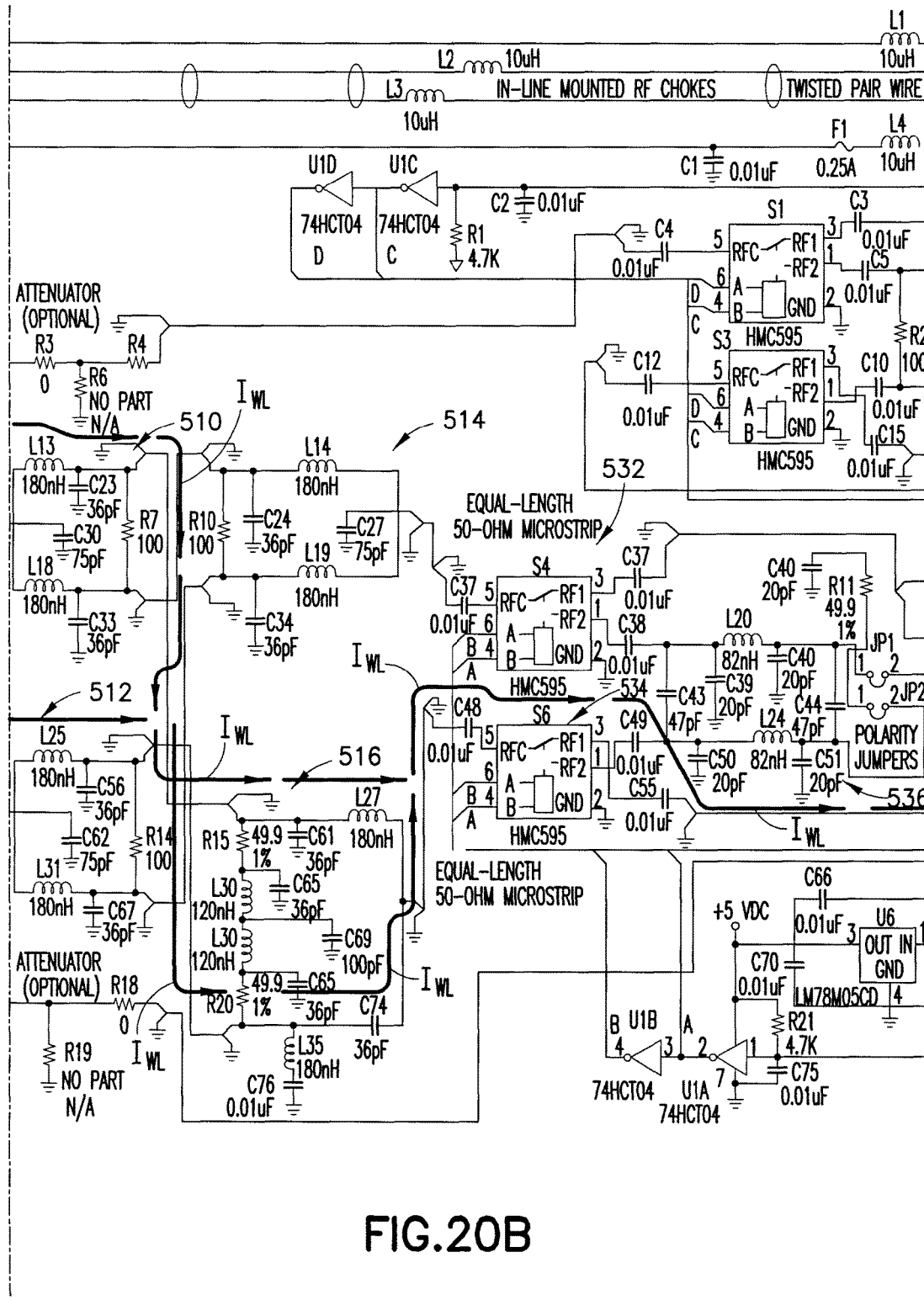
Figure 20C:
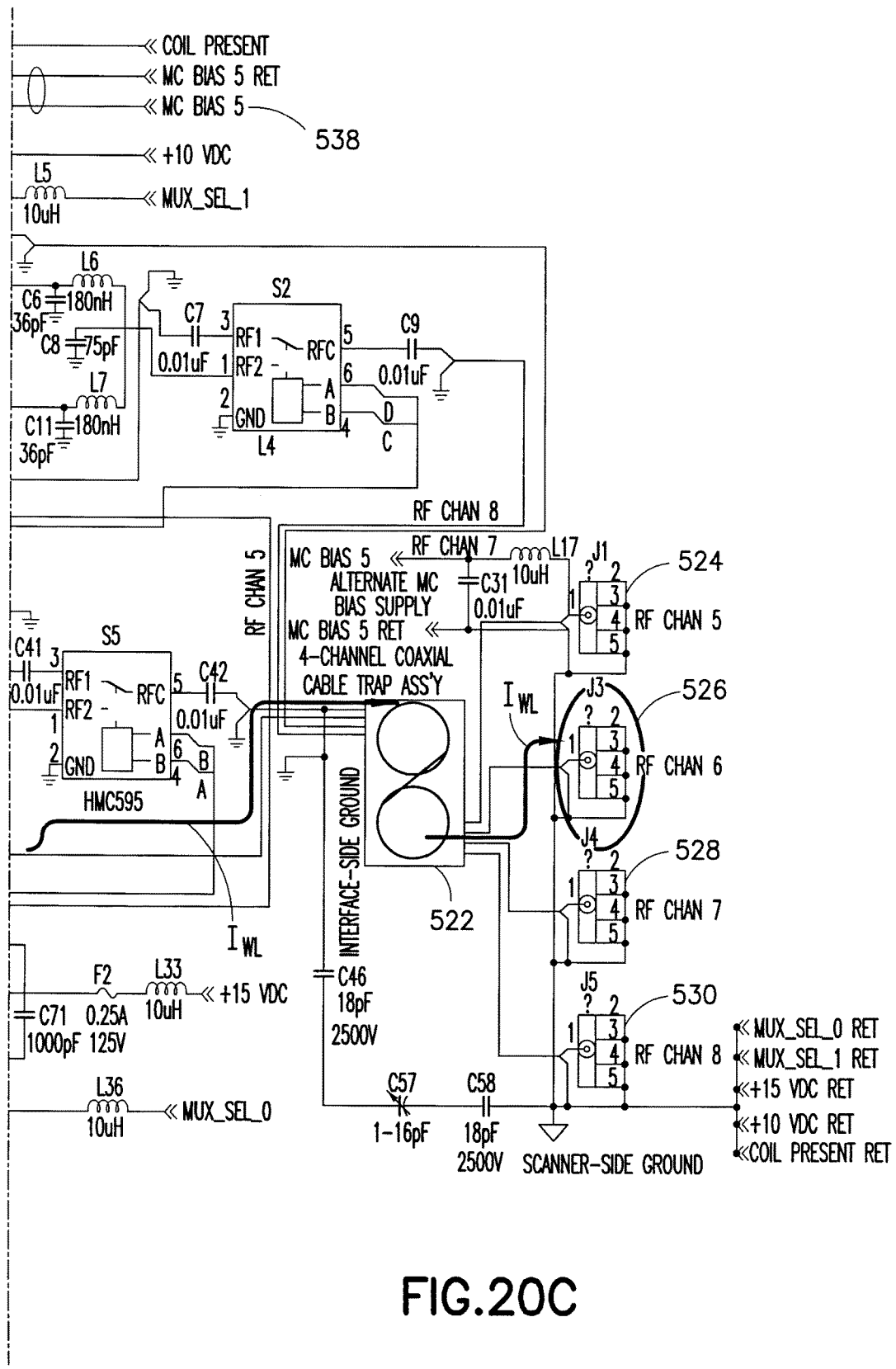

With continued reference to FIGS. 20A-20C, the manner in which interface device 500 processes the voltage signals received from output cables 416 and 418 is now described. Preamplifier networks 502 and 504 each amplify the voltage signals they receive and pass the resulting amplified versions to first and second power splitter networks 506 and 508, respectively. The signals from the first and second power splitter networks 506 and 508 are then sent to third and fourth power splitter networks 510 and 512 such that the signals produced thereby are subsequently sent to the 0 degree combining network 516. Because the horizontal voltage signals received from power splitter networks 506 and 508 are in phase, zero degree combining network 516 is able to constructively combine them. Simultaneously, zero degree combining network 516 also cancels the 90 degree vertical voltage signals received from power splitter network 506 with the −90 degree vertical voltage signals received from power splitter network 508. This yields a whole loop signal that is fed through switching network 534 to cable trap 522. Cable trap 522 directs the signal to the second output channel 526. The flow of current through interface device 500 when in Whole Loop mode is shown by arrows $I_{WL}$ in FIGS. 20A-20C.

Whole Saddle Mode

Figure 21:
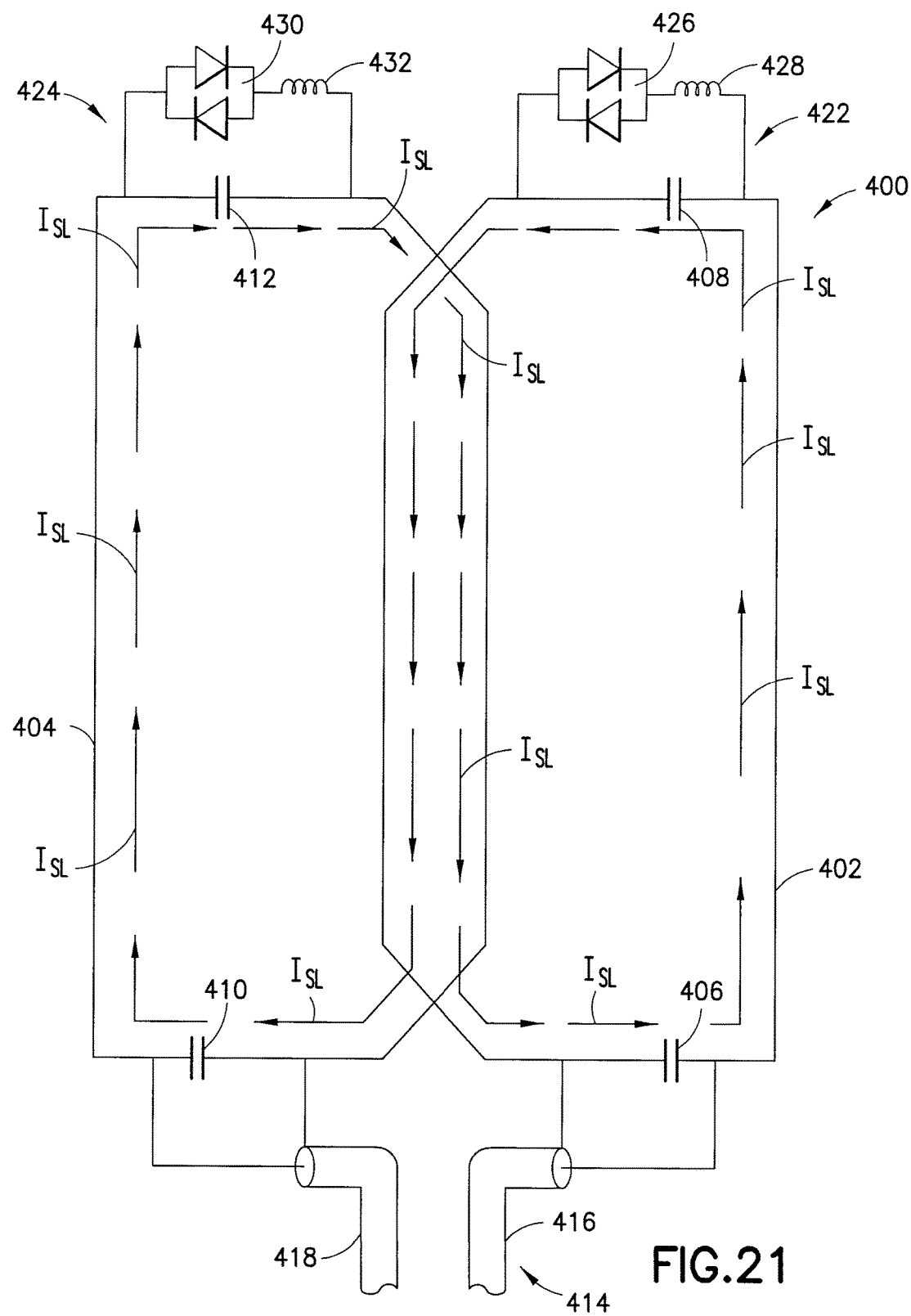
FIG. 21 is a schematic diagram of the coil of FIG. 12 illustrating the manner in which current is induced therein when in Saddle Loop mode.

With reference to FIGS. 21 and 22A-22C, the operation of coil 400 and interface device 500 when in Whole Saddle mode will now be described. As shown in FIG. 21, during the receive cycle, coil 400 is also capable of emulating a butterfly-type or saddle-type coil for detecting MR signals oriented parallel to the plane of coil 400. The tuning scheme of coil 400 allows for a simple loop current path for an outer loop as discussed hereinabove with reference to the Whole Loop mode but also alternative current paths, involving counter-rotating currents, for the outer loop, the right edge of the second coil loop 404, and the left edge of the first coil loop 402 in various combinations. One of these combinations is the Whole Saddle mode as shown in FIG. 21. The flow of current through the coil in Whole Saddle mode is illustrated by arrows $I_{SL}$ in FIG. 21.

Figure 2A:
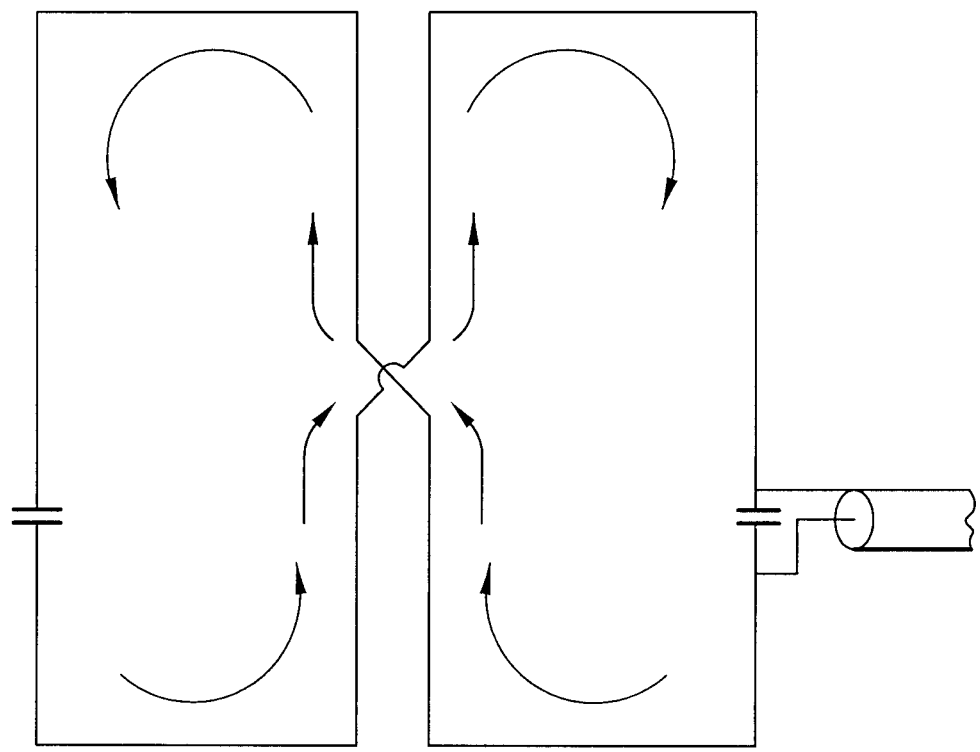
FIG. 2A is a schematic diagram of a conventional butterfly coil and FIG. 2B is a representation of the horizontally oriented magnetic fields it is capable of sensing.
Figure 2B:
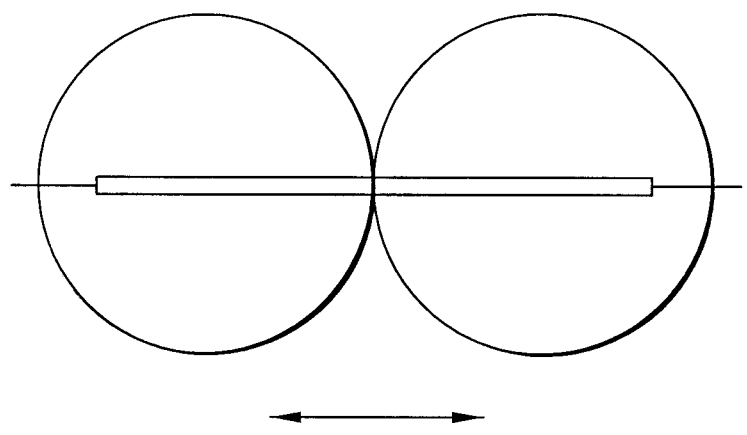
Figure 3:
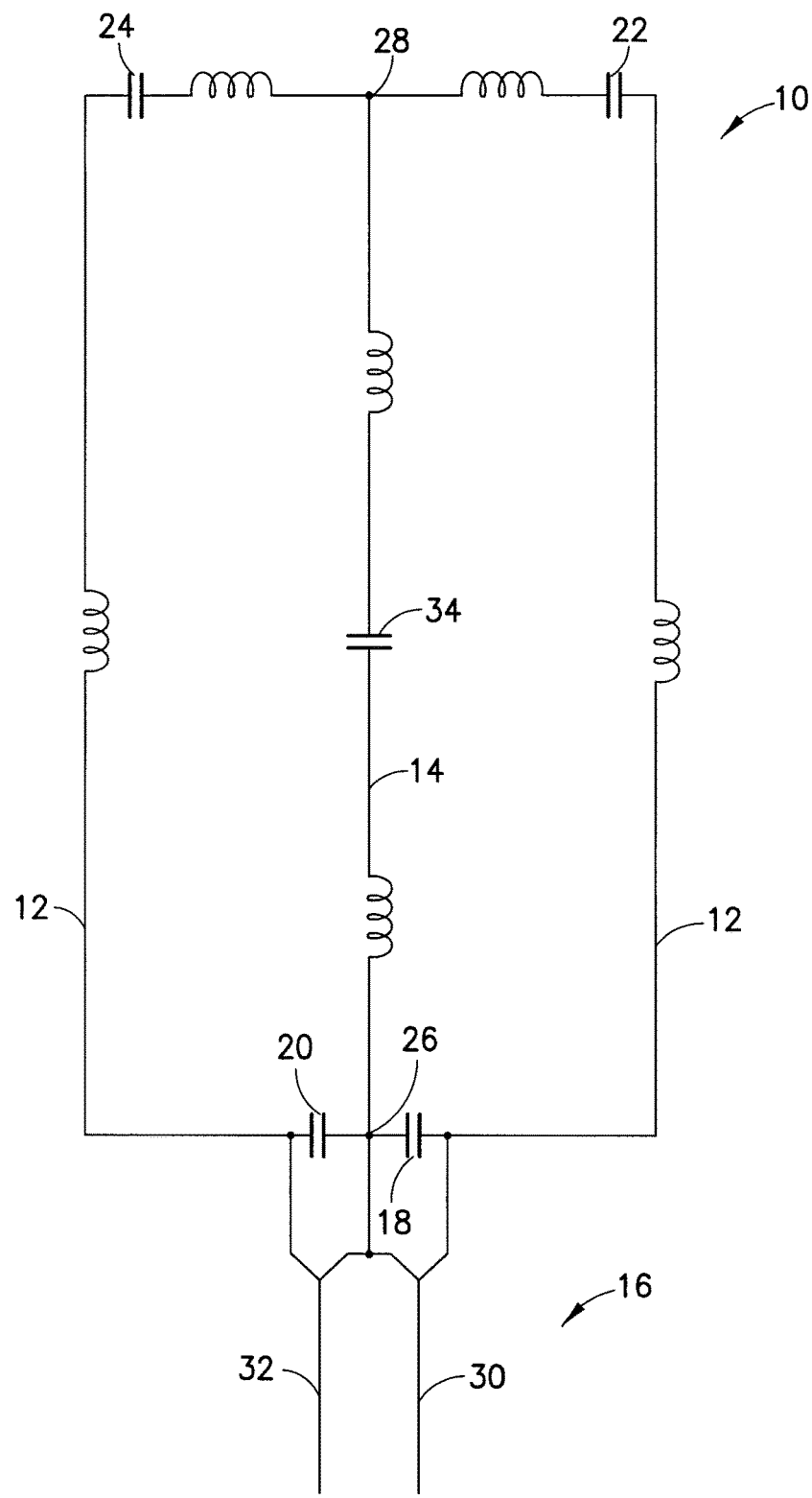
FIG. 3 is a schematic diagram of a conventional quadrature endorectal coil.
Figure 4:
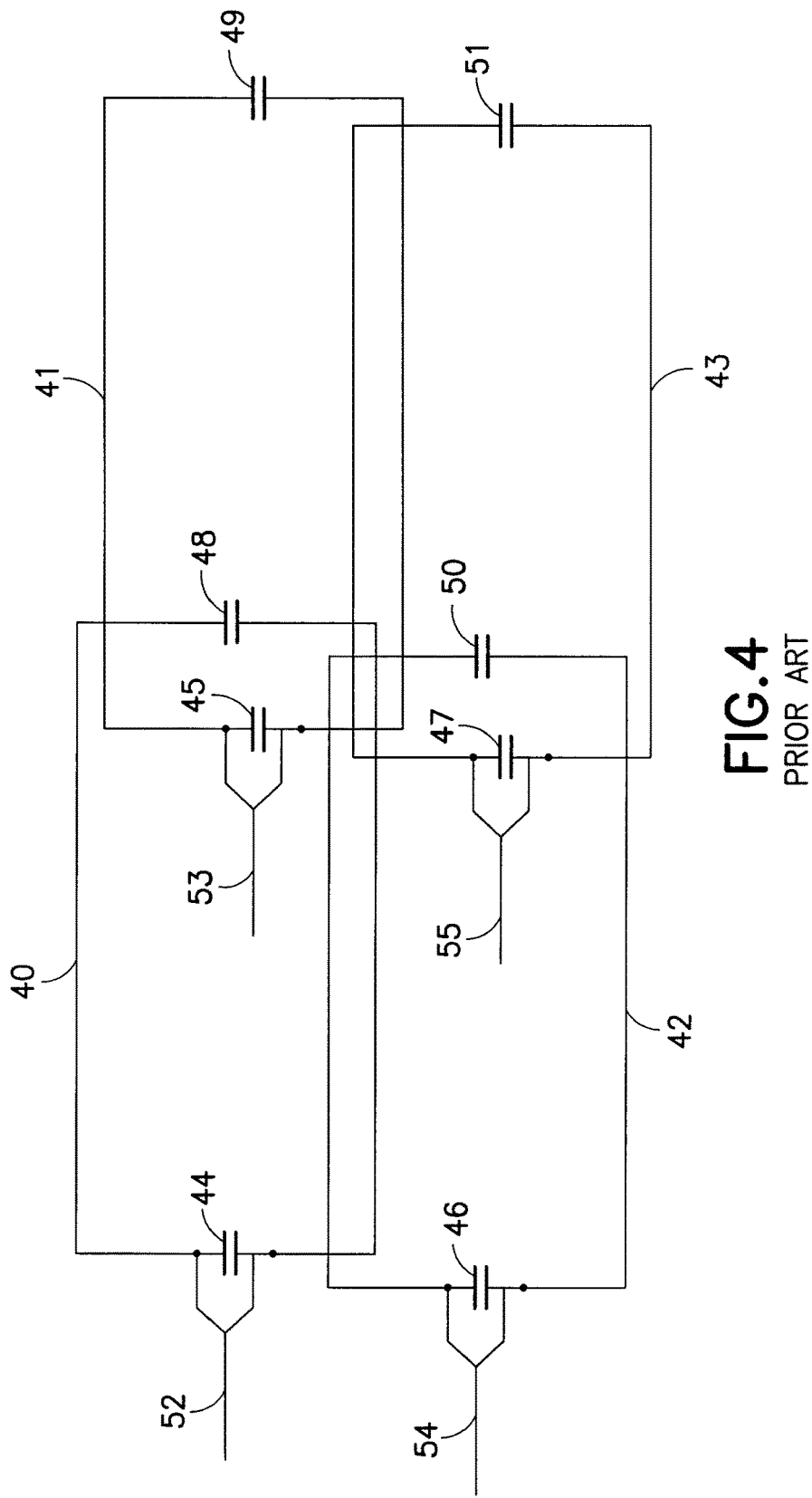
FIG. 4 is a schematic diagram of a conventional four channel phased array endorectal coil whose loops are partially overlapped.

Accordingly, although not physically formed by twisting a conductive loop in the middle to form two subloops about a midpoint as is the case with prior art saddle coils, such as the coil illustrated in FIG. 2A, the coil structure of the present invention, nevertheless electrically emulates the operation of a saddle coil.

The phase of the "vertical" voltage signals detectable across the drive capacitor 406 of first coil loop 402 at the first coaxial cable 416 is 180 degrees out of phase with the "vertical" voltage signals detectable across the drive capacitor 410 of the second coil loop 404 at the second coaxial cable 418. The significance of this 180 degree phase differential becomes apparent in connection with the operation of interface device 500 discussed below.

Figures 22, 22A:
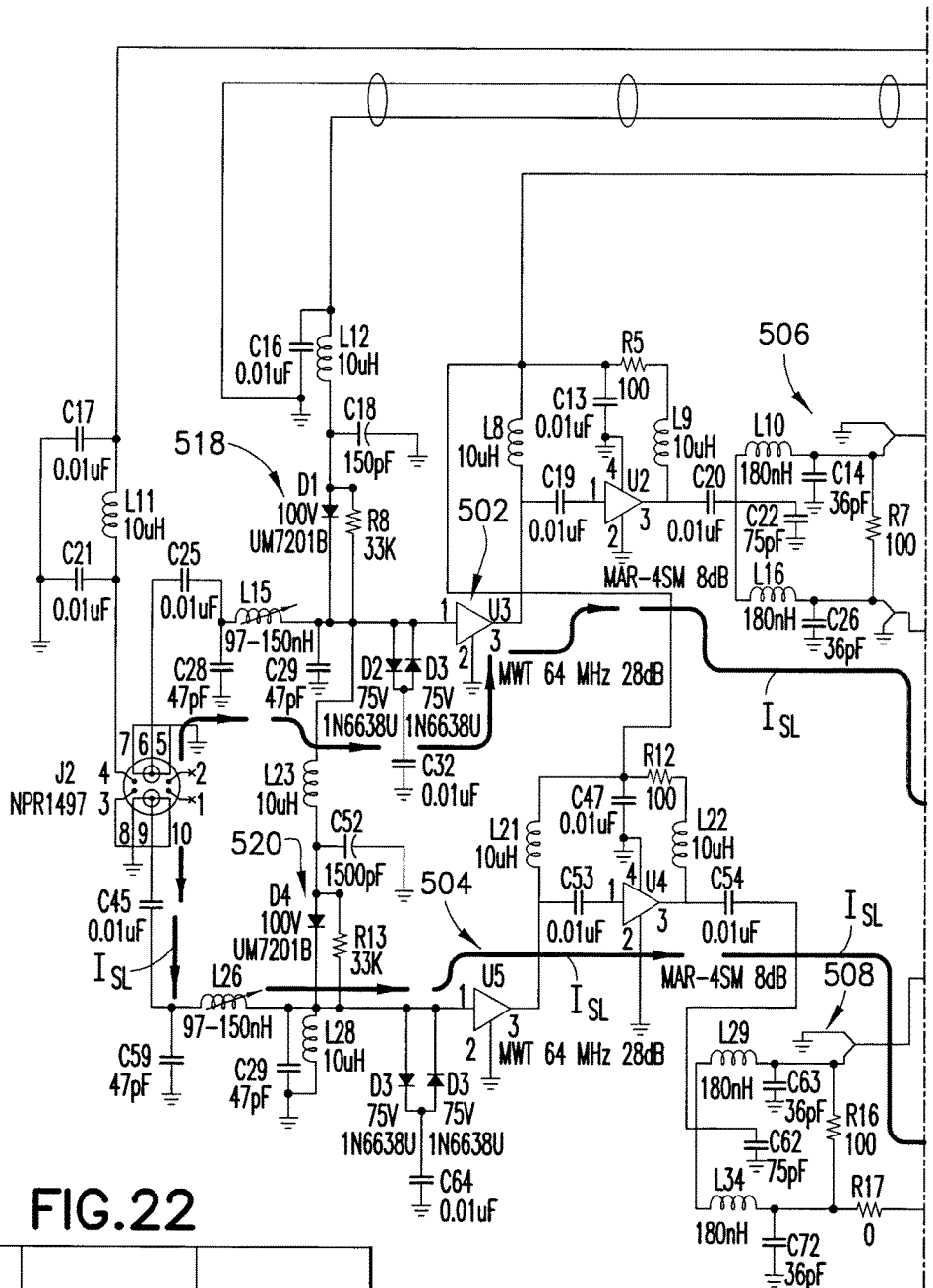
FIG. 22 is made up of FIGS. 22A, 22B, and 22C.
FIGS. 22A-22C form a schematic diagram of the interface device of FIG. 14 illustrating the manner in which the interface device operates when in Saddle Loop mode.
Figure 22B:
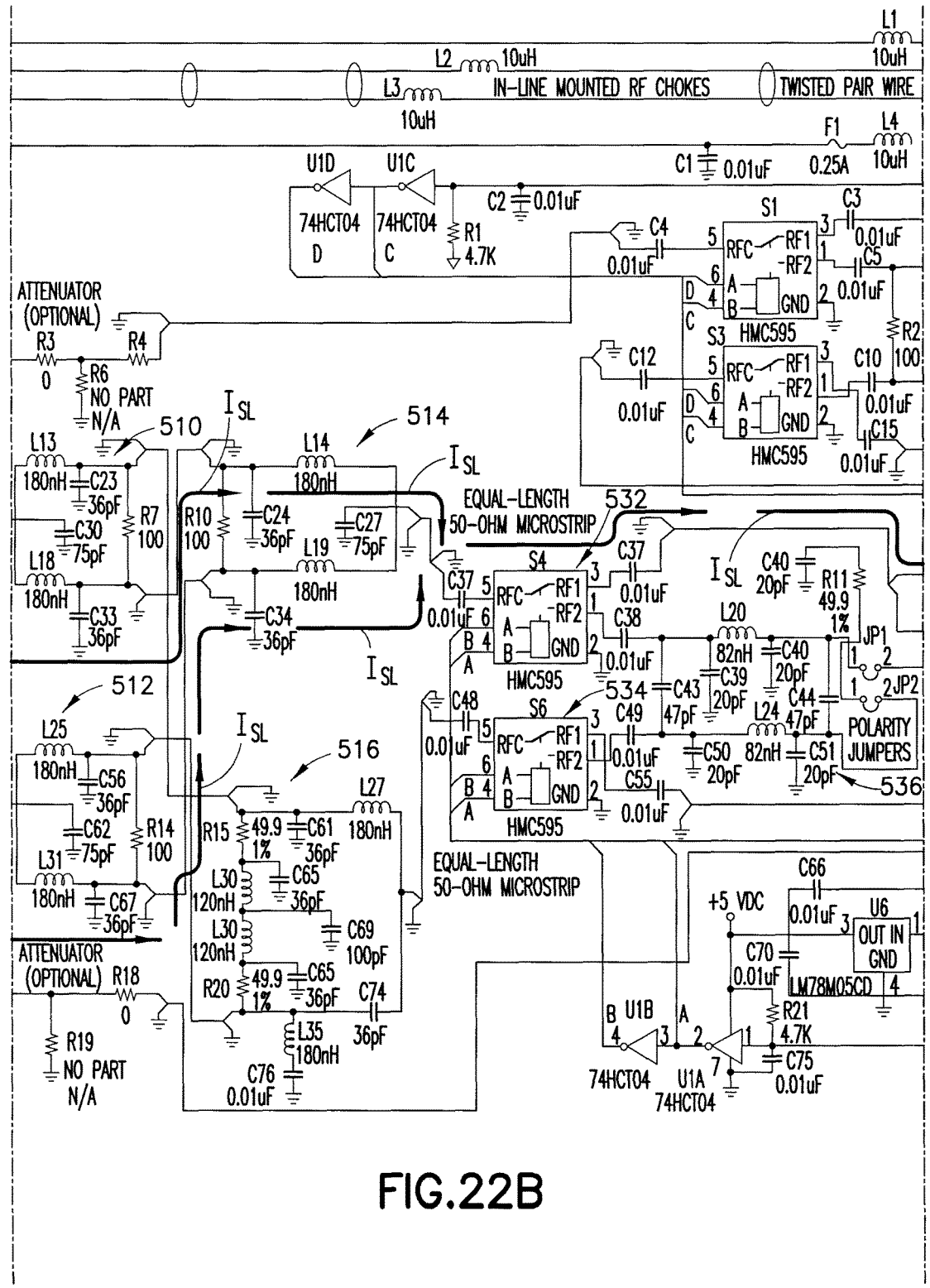
Figure 22C:
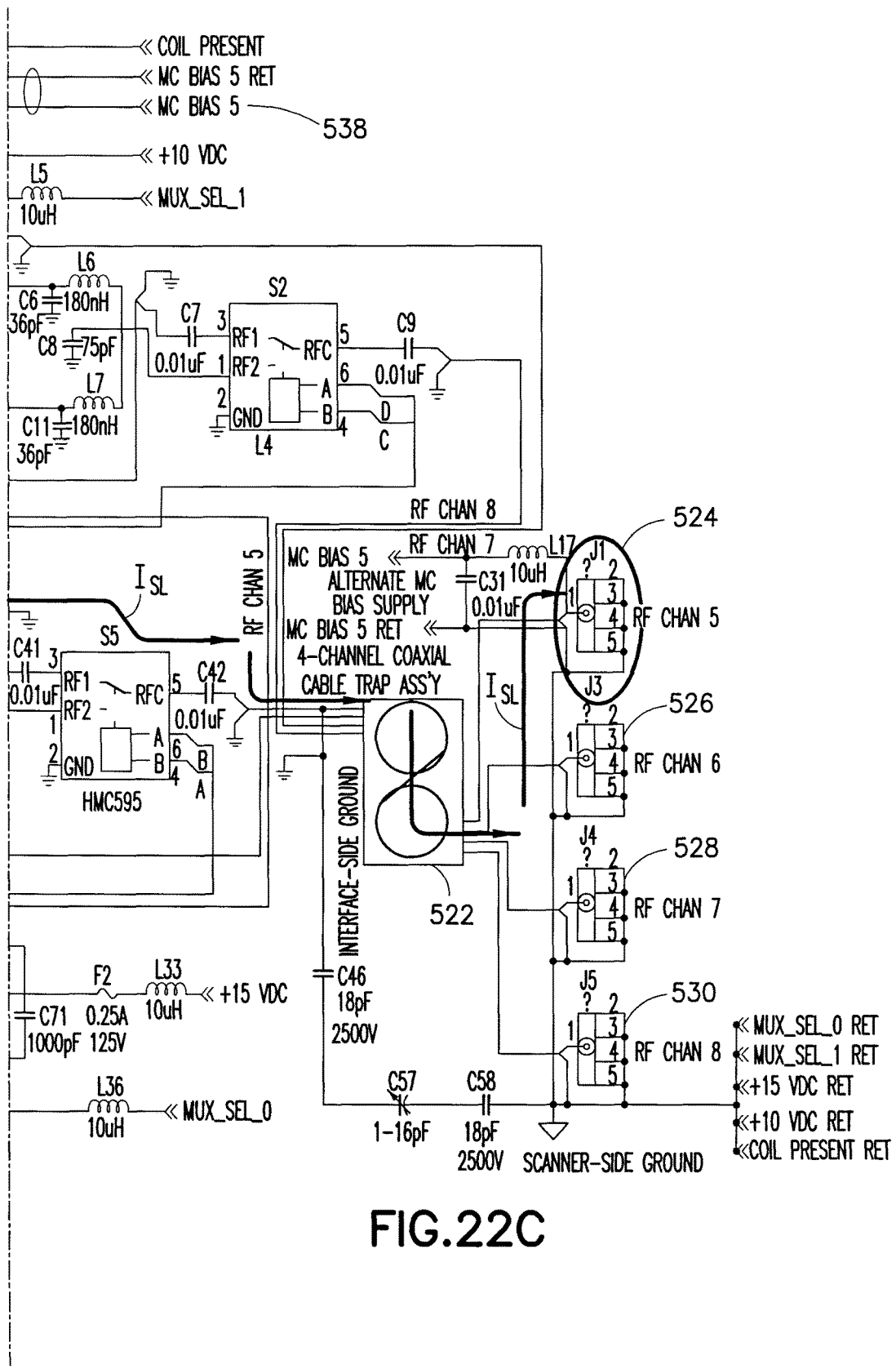

Having completed discussion of the manner in which current flows through coil 400 during a receive cycle when in Whole Saddle mode, a description of the operation of interface device 500 during the receive cycle of the MR system when in Whole Saddle mode will now be described with specific reference to FIGS. 22A-22C. Coil 400 outputs voltage signals representative of MR signals of both horizontal and vertical orientation.

The manner in which interface device 500 processes the voltage signals received from the first and second coaxial cables 416 and 418 is now described. The preamplifier networks 502 and 504 each amplify the voltage signals they receive and pass the resulting amplified versions to the first and second power splitter networks 506 and 508, respectively. The signals from the first and second power splitter networks 506 and 508 are then sent to third and fourth power splitter networks 510 and 512 such that the signals produced thereby are subsequently sent to the 180 degree combining network 514. Because the vertical voltage signals received from power splitter networks 510 and 512 are out of phase by 180 degrees, 180 degree combining network 514 is able to constructively combine them. 180 degree combining network 514 cancels the horizontal voltage signals received from power splitter network 510 with the horizontal voltage signals received from power splitter network 512 because they are received in phase. This yields a saddle loop signal that is fed through switching network 532 to cable trap 522. Cable trap 522 directs the signal to the first output channel 524. The flow of current through interface device 500 when in Saddle mode is shown by arrows $I_{SL}$ in FIGS. 22A-22C.

Whole Loop and Whole Saddle Mode

The operation of coil 400 and interface device 500 when in Whole Loop and Whole Saddle mode, will now be described. During the receive cycle, when operating in Whole Loop and Whole Saddle mode, coil 400 operates in the same manner as described hereinabove for both the Whole Loop and Whole Saddle modes. However, interface device 500 functions in a slightly different manner Instead of ignoring the output of the first channel 524 as in the Whole Loop mode or ignoring the output of the second channel 526 as in the Whole Saddle mode, a 2-channel signal is provided to the host scanner representing both the Whole Loop and the Whole Saddle signal, as described hereinabove, and is provided to the third output channel 528 and the fourth output channel 530, respectively. Accordingly, a 2-channel signal is provided to the host scanner.

Right Loop, Left Loop, Whole Loop, Whole Saddle or LLLS Mode

The operation of coil 400 and interface device 500 when in Right Loop, Left Loop, Whole Loop, Whole Saddle, or LLLS mode, will now be described. During the receive cycle, when operating in LLLS mode, coil 400 operates in the same manner as described hereinabove for each of the Right Loop, Left Loop, Whole Loop, and Whole Saddle modes. In addition, the interface device 500 is configured to provide each of these signals to the host scanner such that a 4-channel output is provided to the host scanner of the MR system.

Loop/Saddle Spectroscopy Mode

The operation of coil 400 and interface device 500 when in Loop/Saddle Spectroscopy mode, will now be described. During the receive cycle, when operating in Whole Loop and Whole Saddle modes, coil 400 operates in the same manner as described hereinabove for both the Whole Loop and Whole Saddle modes. However, interface device 500 functions in a slightly different manner. The manner in which interface device 500 processes the voltage signals received from output cables 416 and 418 when in Loop/Saddle Spectroscopy mode is now described. Preamplifier networks 502 and 504 each amplify the voltage signals they receive and pass the resulting amplified versions to first and second power splitter networks 506 and 508, respectively. The signals from the first and second power splitter networks 506 and 508 are then sent to third and fourth power splitter networks 510 and 512 such that the signals produced thereby are subsequently sent to the 0 degree combining network 516 and the 180 degree combining network 514. The signals from the combining networks 514 and 516 are then fed through switching networks 532 and 534. The switching networks 532 and 534 direct the signals to the 90 degree combining network 536, the output of which is sent to the cable trap 522. Cable trap 522 directs the signal to the first output channel 524.

While interface device 500 was described hereinabove as being used with coil 400, interface device 500 could be used with any of coils 100, 200, and 300 to yield the above described modes.

Accordingly, the present invention allows for a two element coil layout, such as coils 100, 200, 300, and 400, that can produce two loops or a whole loop and whole saddle combination based on the power splitter and combiner networks provided in the interface device 500. In addition, these unique field patterns can be obtained separately to provide four unique channels which have unique radiation patterns. In addition, various steps have been taken to reduce ghosting artifacts while still achieving a high signal-to-noise ratio. With reference to FIG. 23, a graph illustrating the signal-to-noise ratio of various coils discussed hereinabove is provided. The current prior art coil, such as the coil illustrated in FIG. 1A, provides the lowest signal-to-noise ratio as shown by line 600. While the common conductor design of the coil 100 of FIG. 6 shows an improved signal-to-noise ratio as shown by line 610, this increase was not as high as desired. Accordingly, the design for coil 400 of FIG. 12 was reached and provided a much higher signal-to-noise ratio as shown by line 620. However, ghosting artifacts were produced in images created by this coil. Accordingly, it was discovered that reducing the preamplifier power supply from 10V to 5V would reduce the ghosting artifacts. While this slightly reduces the signal-to-noise ratio achieved by the coil, it still has a higher signal-to-noise ratio than both the conventional coil and the common conductor coil 100 as shown by line 630.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements. For example, it is to be understood that the present invention contemplates that, to the extent possible, one or more features of any embodiment can be combined with one or more features of any other embodiment.

Accordingly, to promote the progress of science and the useful arts, the inventor(s) hereby secure by Letters Patent exclusive rights to all subject matter embraced by the following claims for the time prescribed by the Patent Act.

The invention claimed is:

1. An interface device for interfacing a coil with a magnetic resonance system, the coil comprising a pair of coil loops arranged in a phased array configuration each of which for receiving magnetic resonance signals from a region of interest corresponding thereto, the interface device comprising:
   (a) a first preamplifier for receiving a signal from a first coil loop of the pair of coil loops to produce a first amplified signal;
   (b) a second preamplifier for receiving a signal from a second coil loop of the pair of coil loops to produce a second amplified signal;
   (c) a first splitter operatively connected to the first preamplifier for dividing the first amplified signal into a right loop signal that is provided to a first channel output and a first composite signal;
   (d) a second splitter operatively connected to the second preamplifier for dividing the first amplified signal into a left loop signal that is provided to a second channel output and a second composite signal;
   (e) a third splitter operatively connected to the first splitter for dividing the first composite signal;
   (f) a fourth splitter operatively connected to the second splitter for dividing the second composite signal;
   (g) a zero degree combiner operatively connected to the third splitter and the fourth splitter for combining signals received therefrom to produce a saddle signal that is provided to a third channel output; and
   (h) a 180 degree combiner operatively connected to the third splitter and the fourth splitter for combining signals received therefrom to produce a whole loop signal that is provided to a fourth channel output,
   wherein the interface device is configured to selectively recognize each of the first, second, third, and fourth channel outputs, thereby allowing the magnetic resonance system coupled to the interface device to produce images in a plurality of different modes.

2. The interface device of claim 1, wherein the first preamplifier and the second preamplifier are provided with a predetermined reduced supply voltage as compared to a rated supply voltage of the first preamplifier and the second preamplifier.

3. The interface device of claim 1, further comprising at least one attenuator providing an attenuation nominally in the range of 3 dB to 6 dB, the at least one attenuator positioned at at least one of (a) between the first preamplifier and the first splitter; (b) between the second preamplifier and the second splitter; (c) after the first splitter; and (d) after the second splitter.

4. The interface device of claim 1, wherein the plurality of modes include: Left Loop; Right Loop; Whole Loop; Whole Saddle; Right Loop and Left Loop (LL); Whole Loop and Whole Saddle; and Right Loop, Left Loop, Whole Loop, and Whole Saddle (LLLS).

5. A system for obtaining images of a region of interest, the system comprising:
   (a) an intracavity probe comprising:
      (i) a pair of coil loops arranged in a phased array configuration each of which receives magnetic resonance signals from the region of interest corresponding thereto, each of the coil loops having a drive capacitor and a tuning capacitor with the tuning capacitor having a value selected to resonate the coil loop corresponding thereto at an operating frequency of a magnetic resonance system;
      (ii) a pair of output cables each of which is connected at a first end thereof across the drive capacitor of one of the coil loops such that each of the drive capacitors is provided with a separate ground; and
      (iii) a spacer material positioned adjacent to an anterior surface of the pair of the coil loops, the spacer material enabling a predetermined distance of between about 0.03 and about 0.06 inches to exist between the pair of coil loops and the region of interest and thereby reduces intensity of the magnetic resonance signals in proximity of the coil loops, maintains a signal-to-noise ratio at a depth within the region of interest appropriate to reconstruct the images of the region of interest, and reduces artifacts in the images inclusive of the Gibbs artifact when the intracavity probe is inserted into a cavity of a patient during acquisition of the images; and
   (b) an interface device for interfacing the intracavity probe with the magnetic resonance system, the interface device comprising:
      (i) a first preamplifier for receiving a signal from a first coil loop of the pair of coil loops to produce a first amplified signal;
      (ii) a second preamplifier for receiving a signal from a second coil loop of the pair of coil loops to produce a second amplified signal;
      (iii) a first splitter operatively connected to the first preamplifier for dividing the first amplified signal into a right loop signal and a first composite signal;
      (iv) a second splitter operatively connected to the second preamplifier for dividing the first amplified signal into a left loop signal and a second composite signal;
      (v) a third splitter operatively connected to the first splitter for dividing the first composite signal;
      (vi) a fourth splitter operatively connected to the second splitter for dividing the second composite signal;
      (vii) a zero degree combiner operatively connected to the third splitter and the fourth splitter for combining signals received therefrom to produce a saddle signal; and
      (viii) a 180 degree combiner operatively connected to the third splitter and the fourth splitter for combining signals received therefrom to produce a whole loop signal.

6. The system of claim 5, wherein the first preamplifier and the second preamplifier are provided with a predetermined reduced supply voltage as compared to a rated supply voltage of the first preamplifier and the second preamplifier.

7. The system of claim 5, wherein the intracavity probe further comprises a pair of decoupling circuits each of which is connected across the tuning capacitor of one of the coil loops.

8. The system of claim 7, wherein each of the decoupling circuits is an active decoupling circuit.

9. The system of claim 7, wherein each of the decoupling circuits is a passive decoupling circuit.

10. The system of claim 7, wherein each of the decoupling circuits includes an active decoupling circuit and a passive decoupling circuit.

11. The system of claim 5, further comprising an intermediate conduit having:
   (a) an input connector;
   (b) an output connector;
   (c) a pair of internal cables for connecting at one end thereof, respectively, to the output cables of the intracavity probe via the input connector and approximate another end thereof to the interface device via the output connector;
   (d) a pair of baluns each of which is interconnected between an end of one of the internal cables and at least one of the input connector and the output connector; and
   (e) at least one cable trap connected thereabout.

12. The system of claim 5, wherein the interface device further comprises at least one attenuator providing an attenuation nominally in the range of 3 dB to 6 dB, the at least one attenuator positioned at at least one of (a) between the first preamplifier and the first splitter; (b) between the second preamplifier and the second splitter; (c) after the first splitter; and (d) after the second splitter.

13. The system of claim 5, wherein the phased array configuration requires the pair of coil loops to be critically overlapped.

14. The system of claim 5, wherein the phased array configuration requires the pair of coil loops to share a common conductor.

15. The system of claim 5, wherein the phased array configuration requires the pair of coil loops to be arranged in a hybrid overlap configuration wherein at least a portion of each of the coil loops is overlapped and the coil loops share a common conductor.

16. The system of claim 5, wherein a passive decoupling circuit is provided at a second end of each of the output cables.

17. The system of claim 16, wherein each of the passive decoupling circuits comprises series connected back-to-back diodes and a reactance component.

18. The system of claim 17, wherein the reactance component is at least one of an inductor and a capacitor.

* * * * *